United States Patent
Dai et al.

(10) Patent No.: US 11,771,699 B2
(45) Date of Patent: Oct. 3, 2023

(54) COMBINED TREATMENT WITH A TLR7 AGONIST AND AN HBV CAPSID ASSEMBLY INHIBITOR

(71) Applicant: Hoffmann-La Roche Inc., Little Falls, NJ (US)

(72) Inventors: Lue Dai, Shanghai (CN); Lu Gao, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/705,577

(22) Filed: Sep. 15, 2017

(65) Prior Publication Data
US 2018/0000824 A1 Jan. 4, 2018

Related U.S. Application Data

(63) Continuation of application No. PCT/EP2016/055484, filed on Mar. 15, 2016.

(30) Foreign Application Priority Data

Mar. 16, 2015 (WO) ................. PCT/CN2015/074269
Mar. 23, 2015 (WO) ................. PCT/CN2015/074854
(Continued)

(51) Int. Cl.
*A61K 31/519* (2006.01)
*A61K 31/506* (2006.01)
(Continued)

(52) U.S. Cl.
CPC .......... *A61K 31/519* (2013.01); *A61K 31/216* (2013.01); *A61K 31/381* (2013.01);
(Continued)

(58) Field of Classification Search
CPC .. A61K 31/40; A61K 31/506; A61K 31/5355; A61K 31/7064; A61K 31/216;
(Continued)

(56) References Cited

U.S. PATENT DOCUMENTS 5,041,426 A 8/1991 Robins et al.
5,476,659 A 12/1995 Goodman et al.
(Continued)

FOREIGN PATENT DOCUMENTS

CN 101212968 A 7/2008
CN 101516192 A 8/2009
(Continued)

OTHER PUBLICATIONS

M. H. Cho et al. (First published, Dec. 25, 2013, Journal of viral Hepatitis, 2013, 21, 843-852, https://doi.org/10.1111/jvh. 12214; 2-Amino-N -(2,6-dichloropyridin-3-yl)Acetamide derivatives as a novel class of HBV capsid assembly inhibitor).*
(Continued)

*Primary Examiner* — Theodore R. Howell
(74) *Attorney, Agent, or Firm* — Genentech, Inc.; Richard G. A. Bone

(57) ABSTRACT

The present invention is directed to compositions and methods for treating hepatitis B virus infection. In particular, the present invention is directed to a combination therapy comprising administration of a TLR7 agonist and an HBV capsid assembly inhibitor for use in the treatment of chronic hepatitis B patient.

32 Claims, 11 Drawing Sheets

Specification includes a Sequence Listing.

(30) Foreign Application Priority Data

Jul. 20, 2015 (WO) ................ PCT/CN2015/084480
Feb. 18, 2016 (WO) ................ PCT/CN2016/074012

(51) Int. Cl.
| | |
|---|---|
| A61K 31/40 | (2006.01) |
| A61K 31/5355 | (2006.01) |
| A61K 31/7064 | (2006.01) |
| A61P 31/20 | (2006.01) |
| A61P 1/16 | (2006.01) |
| A61K 31/216 | (2006.01) |
| A61K 31/381 | (2006.01) |
| A61K 31/426 | (2006.01) |

(52) U.S. Cl.
CPC ............ *A61K 31/40* (2013.01); *A61K 31/426* (2013.01); *A61K 31/506* (2013.01); *A61K 31/5355* (2013.01); *A61K 31/7064* (2013.01); *A61P 1/16* (2018.01); *A61P 31/20* (2018.01); *A61K 2300/00* (2013.01)

(58) Field of Classification Search
CPC .. A61K 31/381; A61K 31/426; A61K 31/519; A61K 2300/00; A61P 1/16; A61P 31/12; A61P 31/20
USPC .................................................. 514/259, 269
See application file for complete search history.

(56) References Cited

U.S. PATENT DOCUMENTS

| | | | | |
|---|---|---|---|---|
| 7,560,544 | B2* | 7/2009 | Webber ................ | C07D 513/04 536/27.2 |
| 7,709,448 | B2* | 5/2010 | Haley ................ | C07D 513/04 514/42 |
| 9,233,978 | B2* | 1/2016 | Guo ........................ | A61P 31/12 |
| 9,266,904 | B2* | 2/2016 | Guo ........................ | A61P 31/12 |
| 9,441,008 | B2* | 9/2016 | Chen ...................... | A61P 31/20 |
| 9,447,086 | B2* | 9/2016 | Guo ...................... | C07D 417/14 |
| 9,758,530 | B2* | 9/2017 | Guo ...................... | C07D 491/18 |
| 10,040,815 | B2* | 8/2018 | Chen ...................... | A61P 43/00 |
| 10,040,818 | B2* | 8/2018 | Jayaraman ............. | C07K 1/047 |
| 10,081,627 | B2* | 9/2018 | Guo ...................... | C07D 487/04 |
| 10,428,069 | B2* | 10/2019 | Guo ...................... | A61P 31/12 |
| 10,596,173 | B2* | 3/2020 | Gao ...................... | A61K 31/506 |
| 10,618,929 | B2* | 4/2020 | Chen ...................... | A61P 31/14 |
| 2005/0004144 | A1 | 1/2005 | Carson et al. | |
| 2006/0160830 | A1* | 7/2006 | Webber ................... | A61P 25/24 514/260.1 |
| 2007/0072934 | A1 | 3/2007 | Liang et al. | |
| 2008/0032999 | A1 | 2/2008 | Haley et al. | |
| 2010/0216790 | A1 | 8/2010 | Ulrich et al. | |
| 2014/0275167 | A1 | 9/2014 | Hartman | |
| 2015/0252057 | A1 | 9/2015 | Guo et al. | |
| 2019/0298726 | A1* | 10/2019 | Dai ...................... | A61K 31/513 |

FOREIGN PATENT DOCUMENTS

| | | |
|---|---|---|
| CN | 104144913 A | 11/2014 |
| CN | 104650069 A | 5/2015 |
| DE | 10013126 | 9/2001 |
| EP | 0343945 | 11/1989 |
| EP | 1072607 | 1/2001 |
| JP | 6667547 B2 | 2/2000 |
| JP | 2008-534437 A | 8/2008 |
| JP | 2015-506927 A | 3/2015 |
| WO | 89/05649 | 6/1989 |
| WO | 98/16184 | 4/1998 |
| WO | 2001/068641 | 9/2001 |
| WO | 2001/068642 | 9/2001 |
| WO | 2001/068647 | 9/2001 |
| WO | 12005/016235 A2 | 2/2005 |
| WO | 2005/020912 | 3/2005 |
| WO | 2005/025583 | 3/2005 |
| WO | 2005/085462 A1 | 9/2005 |
| WO | 2006/033995 A2 | 3/2006 |
| WO | 2006/033995 A3 | 3/2006 |
| WO | 2006/054177 | 5/2006 |
| WO | 2006/066080 A1 | 6/2006 |
| WO | 2006/134423 | 12/2006 |
| WO | 2007/056527 | 5/2007 |
| WO | 2007/135134 | 11/2007 |
| WO | 2007/143582 | 12/2007 |
| WO | 2009/150002 A2 | 12/2007 |
| WO | 2008/011406 | 1/2008 |
| WO | 2008/090115 A1 | 7/2008 |
| WO | 2008/140549 | 11/2008 |
| WO | 2009/026292 A1 | 2/2009 |
| WO | 2009/067547 A1 | 5/2009 |
| WO | 2009/103176 A1 | 8/2009 |
| WO | 2010/023480 | 3/2010 |
| WO | 2010/069147 A1 | 6/2010 |
| WO | 2012/019426 | 2/2012 |
| WO | 2012/088414 | 6/2012 |
| WO | 2013/052844 | 4/2013 |
| WO | 2013/096744 A1 | 6/2013 |
| WO | 2014/029193 | 2/2014 |
| WO | 2014/037480 A1 | 3/2014 |
| WO | 2014/184328 A1 | 11/2014 |
| WO | 2015/132276 A1 | 9/2015 |
| WO | 2015/172128 | 11/2015 |
| WO | 2016/091698 | 6/2016 |
| WO | 2016-518432 | 6/2016 |
| WO | 2016/146598 A1 | 9/2016 |
| WO | 2018/050571 | 3/2018 |

OTHER PUBLICATIONS

Funk, E. et al. Tickling the TLR7 to cure viral hepatitis. J Transl Med 12, 129 (2014). https://doi.org/10.1186/1479-5876-12-129).*
Allan et al., "Synthesis of analogs of GABA .15. preparation and resolution of some potent cyclopentene and cyclopentane derivatives" Aust. J. Chem 39:855-64 ( 1986).
Asselah et al., "Interferon therapy for chronic hepatitis B" Clin Liver Dis 11:839-849 ( 2007).
Brezillon et al., "Antiviral activity of Bay 41-4109 011 hepatitis B virus in humanized Alb-uPA/SCID mice" PLoSOne 6(12 Suppl 1-6):e25096 (Dec. 2011).
Connolly et al., "New developments in Tool-like receptor targeted therapeutics" Current Opinion in Pharmacology 12:510-518 ( 2012).
Deres et al., "Inhibition of hepatitis B virus replication by drug-induced depletion of nucleocapsids" Science 299(5608):893-6 ( 2003).
Feld et al., "The phenylpropenamide derivative AT-130 blocks HBV replication at the level of viral RNA packaging" Antiviral Res 76:168-177 ( 2007).
Gane et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 ( Nov. 2013).
Grygorenko et al., "Expedient synthesis of cis- and trans-3-aminocyclobutanecarboxylic acids" Synthetic Communications 41:1644-1649 ( 2011).
Guo et al., "Characterization of the intracellular deproteinized relaxed circular DNA of hepatitis B virus: an intermediate of covalently closed circular DNA formation" J Virol 81:12472-12484 ( 2007).
Hemmi et al., "Small anti-viral compounds activate immune cells via the TLR7 MyD88-dependent signaling pathway" Nature Immunology 3(2):196 ( 2002).
Kaisho et al., "Turning NF-kB and IRFs on and off in DC" Trends in Immunology 29(7):329-336 ( 2008).
Mertin et al., "C-Alkylation of functionally substituted carbanions with cyclopropiminium ions: 21 new route to cyclopropane amino acids1" Synlett 2:87-89 ( 1991).
Roethle et al., "Identification and Optimization of Pteridinone Toll-like Receptor 7 (TLR7) Agonists for the Oral Treatment of Viral Hepatitis" Journal of Medicinal Chemistry 56(18):7324-7333 (Sep. 26, 2013).

(56) References Cited

OTHER PUBLICATIONS

Sandstroem et al., "B-Amino acid substitutions and structure-based CoMFA modeling of hepatitis C virus NS3 protease inhibitors" Bioorgan Med Chem 16:5590-5605 ( 2008).

Sells et al., "Production of hepatitis B virus particles in Hep G2 cells transfected with cloned hepatitis B virus DNA" Proc. Natl. Acad. Sci USA 84:1005-1009 ( 1987).

Zlotniek et al., "A small molecule inhibits and misdireets assembly of hepatitis B virus capsids" J Virol 76(10):4848-4854 (May 2002).

Buster, E. H., et al., "Peginterferon alpha-2b is safe and effective in HBeAg-Positive chronic hepatitis B patients with advanced fibrosis" Hepatology 46(2):388-3 94 (Aug. 1, 2007).

Fisicaro, P., et al., "Antiviral intrahepatic T-cell responses can be restored by blocking programmed death-1 pathway in chronic hepatits B" Gastroenterology 138(2):682-693 (Feb. 1, 2010).

Jansen, H.L., et al., "Pegylated interferon alfa-2b alone or in combination with lamivudine for HBeAg-positive chronic hepatitis B: a randomised trial" Lancet 365(9454):123-129 (Jan. 8, 2005).

Kondo, Y., et al., "Hepatitis B surface antigen could contribute to the immunopathogenesis of hepatitis B virus infection" ISRN Gastroenterol 2013( Suppl 935295): 1-8 (Jan. 16, 2013).

Kondo, Y., et al., "Recovery of functional cytotoxic T lymphocytes during lamivudine therapy by acquiring muti-specificity" J Med Virol 74(3):425-433 (Nov. 1, 2004).

Lambert, C.R., et al., "Posttranslational N-glycosylation of the hepatitis B virus large envelope protein" Virol J 4(45):1-9 (May 30, 2007).

Marcellin, P., et al., "Peginterferon alfa-2a alone, lamivudine alone, and the two in combination in patients with HBeAg-negative chronic hepatitis B" N Engl J Med 351(12):1206-1217 (Sep. 16, 2004).

Nayerina, R., et al., "HLA A2 restricted cytotoxic T lymphocyte responses to multiple hepatitis B surface antigen epitopes during hepatitis B virus infection" J Immunol 150(10):4659-4671 (May 15, 1993).

Op Den Brouw, M., et al., "Hepatitis B virus surface antigen impairs myeloid dendritic cell function: a possible immune escape mechanism of hepatitis B virus" Immunology [British] 126(2):280-289 (Feb. 1, 2009).

Shi, C.C., et al., "Hepatitis B virus suppresses the functional interaction between natural killer cells and plasmacytoid dendritic cells" J Viral Hepat 19(2):e26-e33 (Feb. 1, 2012).

Woltman, A.M., et al., "Hepatitis B virus lacks immune activating capacity, but actively inhibits plasmacytoid dendritic cell function" PLoS One 6(1 Suppl 1-14):e15324 (Jan. 5, 2011).

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Hepatitis B virus

<400> SEQUENCE: 1
aagaaaaacc ccgcctgtaa                                           20

<210> SEQ ID NO 2
<211> LENGTH: 23
<212> TYPE: DNA
<213> ORGANISM: Hepatitis B virus

<400> SEQUENCE: 2
cctgttctga ctactgcctc tcc                                       23
```

```
<210> SEQ ID NO 3
<211> LENGTH: 27
<212> TYPE: DNA
<213> ORGANISM: Hepatitis B virus

<400> SEQUENCE: 3
cctgatgtga tgttctccat gttcagc                                    27
```

COMBINED TREATMENT WITH A TLR7 AGONIST AND AN HBV CAPSID ASSEMBLY INHIBITOR

RELATED APPLICATIONS

This application is a Continuation application of International Application No. PCT/EP2016/055484, filed Mar. 15, 2016, claiming priority to Application No. PCT/CN2015/074269, filed Mar. 16, 2015, Application No. PCT/CN2015/074854, filed Mar. 23, 2015, Application No. PCT/CN2015/084480, filed Jul. 20, 2015 and Application No. PCT/CN2016/074012, filed Feb. 18, 2016, each of which are incorporated herein by reference in its entirety.

SEQUENCE LISTING

This application contains a Sequence Listing which has been submitted via EFS-Web and is hereby incorporated by reference in its entirety. Said ASCII copy, created on Sep. 11, 2017, is named Sequence Listing.txt and is 909 bytes in size.

The present invention is directed to compositions and methods for treating hepatitis B virus infection. In particular, the present invention is directed to a combination therapy comprising administration of a TLR7 agonist and an HBV capsid assembly inhibitor for use in the treatment of chronic hepatitis B patient.

FIELD OF THE INVENTION

Chronic infection of Hepatitis B virus (HBV) is a serious public health problem worldwide, with more than 240 million people chronically infected worldwide. HBV belongs to the Hepadnaviridae family of viruses. Following entry into hepatocyte, its viral genome is delivered into nucleus where a covalently closed circular DNA (cccDNA) is formed through DNA repair of partially double-stranded viral genomecccDNA serves as the template for transcription of viral RNAs. Viral pre-genomic RNA interacts with other two viral components, capsid protein and polymerase to form capsid particles where viral DNA replication occurs. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. When a near full-length relaxed circular DNA is formed through reverse-transcription of viral pregenomic RNA, an immature capsid becomes a mature capsid. Most copies of the encapsidated genome efficiently associate with cellular lipids and viral envelope proteins (S, M, and L) for virion assembly and secretion. However, non-infectious particles are also produced that greatly outnumber the infectious virions. These empty, enveloped particles are referred to as subviral particles (SVPs). The S, M, and L envelope proteins are expressed from a single ORF (open reading frame) that contains three different start codons. All three proteins share a 226aa sequence, the S-domain, at their C-termini. S-domain contains the HBsAg epitope (Lambert, C. & R. Prange. *Virol J,* 2007, 4, 45).

Many observations showed that several HBV viral proteins could counteract the initial host cellular response by interfering with the viral recognition signaling system and subsequently the interferon (IFN) antiviral activity. Among these, the excessive secretion of HBV empty subviral particles may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* 1993, 150, 4659-4671; Kondo et al. *Journal of Medical Virology* 2004, 74, 425-433; Fisicaro et al. *Gastroenterology,* 2010, 138, 682-93). Moreover HBsAg has been reported to suppress the function of immune cells such as monocytes, dendritic cells (DCs) and natural killer (NK) cells by direct interaction (Op den Brouw et al. *Immunology,* 2009b, 126, 280-9; Woltman et al. *PLoS One,* 2011, 6, e15324; Shi et al. *J Viral Hepat.* 2012, 19, e26-33; Kondo et al. *ISRN Gasteroenterology,* 2013, Article ID 935295).

HBsAg quantification is a biomarker for prognosis and treatment response in chronic hepatitis B. HBsAg loss and seroconversion is the goal for clinical cure, but is rarely observed in chronically infected patients. Current therapy such as Nucleos(t)ide analogues that inhibit HBV DNA synthesis does not directly affect HBsAg level. Nucleos(t)ide analogs, even with prolonged therapy, have demonstrated very low rates of HBsAg clearance comparable to those observed naturally (Janssen et al. *Lancet,* 2005, 365, 123-9; Marcellin et al. *N. Engl. J. Med.,* 2004, 351, 1206-17; Buster et al. *Hepatology,* 2007, 46, 388-94).

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7, TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. AJ O'Neill, *Current Opinion in Pharmacology* 2012, 12:510-518, P. A. Roethle et al, *J. Med. Chem.* 2013, 56, 7324-7333).

Treatment with an oral TLR7 agonist represents a promising solution to provide greater efficacy with better tolerability. Pegylated IFN-α (PEG-IFN-α) is currently used to treat chronic HBV and is an alternative to potentially lifelong treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion)

is also very infrequent with both PEG-IFN-α and nucleos (t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, *Clin Liver Dis* 2007, 11, 839-849).

HBV Capsid Protein Plays Essential Roles in HBV Replication.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J. Virol.* 2002, 4848-4854).

Now, the standard of clinic cure of HBV infection is the loss and/or seroconversion of HBsAg. Even though PEG-IFN-α and nucleos(t)ide are available to HBV patients, the majority (around or more than 90%) of treated patients fail to achieve this goal, which is mainly due to fact that the current therapies cannot elicit the appearance of neutralizing antibodies against HBsAg (anti-HBs), a sign of resolution of HBV infection, in most chronically infected patients. Hence, there is certainly a medical need for treatments with improved success rate of inducing HBsAg loss and/or seroconversion and promoting the production of anti-HBs.

SUMMARY OF THE INVENTION

The present invention relates to a pharmaceutical composition comprising a TLR7 agonist and an HBV capsid assembly inhibitor, in a pharmaceutically acceptable carrier. The "TLR7 agonist" herein is a compound of formula (I), (II) or any one of the compounds disclosed in patent WO2006/066080, particularly the "TLR7 agonist" herein is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate; [(S)-[(2S,5R)-5-(5-amino-2-oxo-thiazolo[4,5-d]pyrimidin-3-yl)-1,3-oxathiolan-2-yl]-cyclopropyl-methyl] acetate; 5-amino-3-(3'-deoxy-β-D-ribofuranosyl)-3H-thiazolo[4,5-d]pyrimidin-2-one; 5-amino-3-(2'-O-acetyl-3'-deoxy-β-D-ribofuranosyl)-3H-thiazolo[4,5-d]pyrimidin-2-one or 5-amino-3-(3'-deoxy-β-D-ribofuranosyl)-3H,6H-thiazolo[4,5-d]pyrimidin-2,7-dione, or pharmaceutically acceptable salt, enantiomer or diastereomer thereof. The HBV capsid assembly inhibitor herein is a compound of formula (III) or any one of the compounds disclosed in patent WO2014/037480, WO 2014/184328 and WO2015/132276, particularly the HBV capsid assembly inhibitor herein is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; or pharmaceutically acceptable salt, enantiomer or diastereomer thereof.

BRIEF DESCRIPTION OF THE FIGURES

FIG. 2: X-ray crystal structure of Compound 2A-2a.

DETAILED DESCRIPTION OF THE INVENTION

Figure 1:
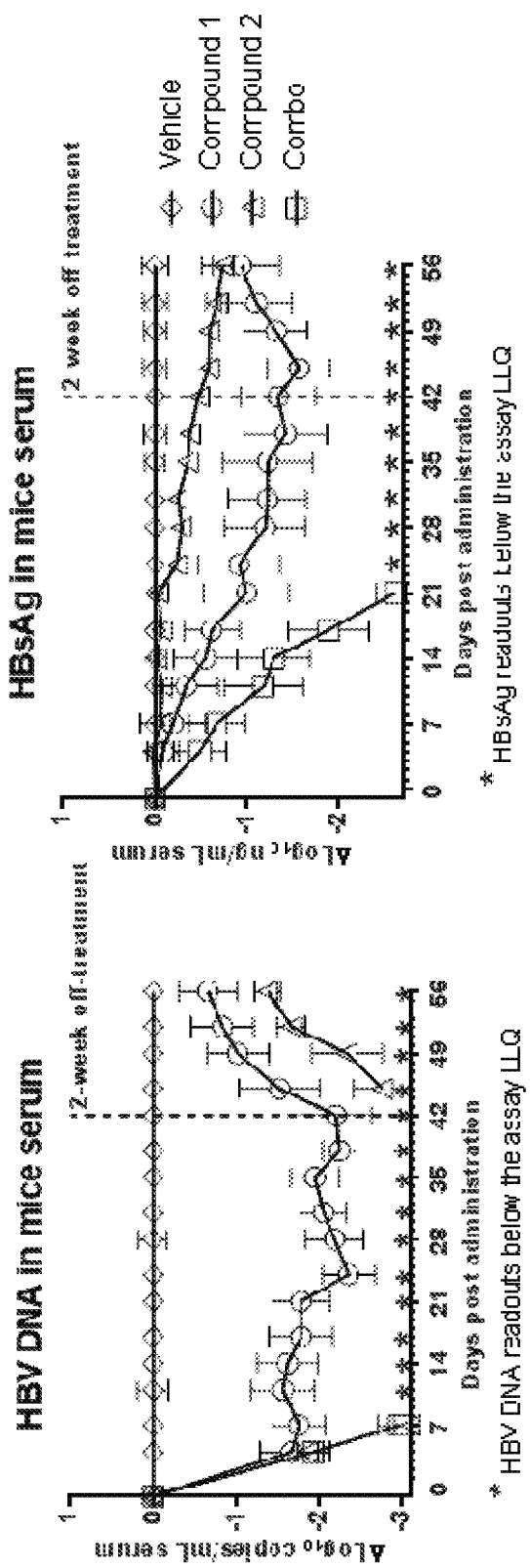
FIG. 1: HBV DNA and HBsAg levels from mice sera in AAV-HBV mouse model. Results were shown in Figure. 1 for mice with sustained level of HBV DNA and HBsAg treated with vehicle (shown as diamond), Compound 1 alone at 100 mg/kg (shown as circle), Compound 2 alone at 12 mg/kg (shown as triangle), or combination of Compound 1 and Compound 2 (shown as square). Relative reduction of HBV DNA and HBsAg post treatment was calculated by normalizing to their levels in the vehicle group as a base line. Synergistic antiviral effect in reducing HBsAg was observed in mice treated with the combination therapy, and more importantly, reduction in HBV DNA and HBsAg was sustained during a 2-week off-treatment period post the combination therapy. LLQ: lower limit of quantification.

Unless defined otherwise, all technical and scientific terms used herein have the same meaning as commonly understood by one of ordinary skill in the art to which this invention pertains.

As used herein, the term "$C_{1-6}$alkyl" refers to a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

As used herein, the term "halo" or "halogen" are used interchangeably herein and refer to fluoro, chloro, bromo, or iodo.

As used herein, the term "$C_{1-6}$alkoxy" refers to a group of $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

As used herein, the term "$C_{3-7}$cycloalkyl" refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

As used herein, the term "$C_{2-6}$alkenyl" refers to an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl.

As used herein, the term "$C_{2-6}$alkynyl" refers to an unsaturated, linear or branched chain alkynyl group containing 2 to 6, particularly 2 to 4 carbon atoms, for example ethynyl, 1-propynyl, propargyl, butynyl and the like. Particular "$C_{2-6}$alkynyl" groups are ethynyl, 1-propynyl and propargyl.

As used herein, the term "heterocyclic" ring or "heterocyclyl" refers to a saturated or partly unsaturated monocyclic or bicyclic ring containing from 3 to 10 ring atoms which can comprise one, two or three atoms selected from nitrogen, oxygen and/or sulfur. Examples of monocyclic heterocyclyl rings containing in particular from 3 to 7 ring atoms include, but not limited to, aziridinyl, azetidinyl, oxetanyl, piperidinyl, piperazinyl, azepinyl, diazepanyl, pyrrolidinyl, morpholinyl, dihydrofuryl, tetrahydrofuryl, tetrahydropyranyl, tetrahydrothiopyranyl and thiomorpholinyl. Bicyclic heterocyclyl can be bicyclic fused ring or bicyclic bridged ring. Examples for bicyclic heterocyclyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl, or difluoroazabicyclo[3.2.1]octyl. Monocyclic and bicyclic heterocyclyl can be further substituted by halogen, $C_{1-6}$alkyl, cyano, carboxy, carboxy$C_{1-6}$alkyl.

The term "heterocyclic amino" refers to an amino group with the nitrogen atom on the heterocyclic ring, wherein "heterocyclic" ring is as defined above.

As used herein, the term "diastereomer" refers to a stereoisomer with two or more centers of chirality and whose molecules are not mirror images of one another. Diastereomers have different physical properties, e.g. melting points, boiling points, spectral properties, activities and reactivities.

As used herein, the term "enantiomers" refers to two stereoisomers of a compound which are non-superimposable mirror images of one another.

As used herein, the term "pharmaceutically acceptable salts" refers to salts which are not biologically or otherwise undesirable. Pharmaceutically acceptable salts include both acid and base addition salts.

As used herein, the term "prodrug" refers to a form or derivative of a compound which is metabolized in vivo, e.g., by biological fluids or enzymes by a subject after administration, into a pharmacologically active form of the compound in order to produce the desired pharmacological effect. Prodrugs are described e.g. in the Organic Chemistry of Drug Design and Drug Action by Richard B. Silverman, Academic Press, San Diego, 2004, Chapter 8 Prodrugs and Drug Delivery Systems, pp. 497-558.

The term "pharmaceutically acceptable acid addition salt" refers to those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" refers to those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

As used herein, "combo" refers to combination.

As used herein, "RT-PCR" refers to Reverse transcription polymerase chain reaction.

As used herein, "CLIA" refers to chemiluminescence immunoassay.

As used herein, "AAV" refers to adeno-associated virus.

As used herein, "AAV-HBV" refers to a recombinant virus that carries 1.3 copies of the HBV genome packaged in AAV capsids. A chronicle HBV infection mouse model can be established by injecting mice with AAV-HBV through tail vein injection. In this mouse model, active HBV replication results in persist HBV viral markers (e.g., HBV DNA, HBsAg, HBeAg, etc.).

As used herein, "HBsAg" refers to hepatitis B surface antigen.

As used herein, "HBeAg" refers to hepatitis B e antigen.

As used herein, "anti-HBs" refers to antibodies against HBsAg.

As used herein, "HBV specific primers" refers to a pair of single-stranded nucleic acid that serves as starting and ending points for specific amplification of HBV DNA regions.

As used herein, "TLR7" refers to the Toll-like receptor 7 of any species of origin (e.g., human, murine, woodchuck etc.).

As used herein, "TLR7 agonist" refers to a compound that acts as an agonist of TLR7. Unless otherwise indicated, a TLR7 agonist can include the compound in any pharmaceutically acceptable form, including any isomer (e.g., diastereomer or enantiomer), salt, solvate, polymorph, and the like. The TLR agonism for a particular compound may be determined in any suitable manner. For example, assays for detecting TLR agonism of test compounds are described, for example, in U.S. Provisional Patent Application Ser. No. 60/432,650, filed Dec. 11, 2002, and recombinant cell lines suitable for use in such assays are described, for example, in U.S. Provisional Patent Application Ser. No. 60/432,651, filed Dec. 11, 2002.

The present invention relates to a pharmaceutical composition comprising a TLR7 agonist and an HBV capsid assembly inhibitor, in a pharmaceutically acceptable carrier.

In one embodiment of present invention, a "TLR7 agonist" is a compound of formula (I):

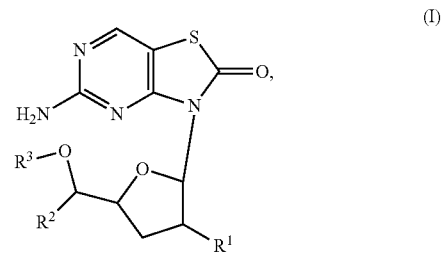

(I)

wherein
$R^1$ is hydroxy, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;
$R^2$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^3$ is hydrogen or $C_{1-6}$alkylcarbonyl;
or pharmaceutically acceptable salt, enantiomer or diastereomer thereof;

In another embodiment of present invention, a "TLR7 agonist" is a compound of formula (II):

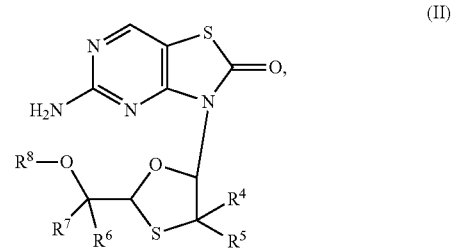

(II)

wherein
$R^4$ and $R^5$ are independently selected from hydrogen, $C_{2-6}$alkenyl and $C_{1-6}$alkyl;
$R^6$ and $R^7$ are independently selected from hydrogen, $C_{1-6}$alkyl, $C_{3-7}$cycloalkyl, $C_{3-7}$cycloalkyl$C_{2-6}$alkynyl, $C_{2-6}$alkenyl, $C_{2-6}$alkynyl and 2-thiophenyl;
$R^8$ is hydrogen or $C_{1-6}$alkylcarbonyl;
or pharmaceutically acceptable salt, enantiomer or diastereomer thereof.

More particularly, the TLR7 agonist according to present invention relates to [(1S)-1-[(2S,4R,5R)-5-(5-amino-2-oxothiazolo[4,5-d]pyrimidin-3-yl)-4-hydroxy-tetrahydrofuran-2-yl]propyl] acetate; [(S)-[(2S,5R)-5-(5-amino-2-oxo-thiazolo[4,5-d]pyrimidin-3-yl)-1,3-oxathiolan-2-yl]-cyclopropyl-methyl] acetate; 5-amino-3-(3'-deoxy-β-D-ribofuranosyl)-3H-thiazolo[4,5-d]pyrimidin-2-one; 5-amino-3-(2'-O-acetyl-3'-deoxy-β-D-ribofuranosyl)-3H-thiazolo[4,5-d]pyrimidin-2-one; 5-amino-3-(3'-deoxy-β-D-ribofuranosyl)-3H,6H-thiazolo[4,5-d]pyrimidin-2,7-dione; or [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate; or pharmaceutically acceptable salt, enantiomer or diastereomer thereof. In another embodiment, a "TLR7 agonist" also relates to anyone of the compounds disclosed in patent WO2006/066080. After administration, compounds of formula (I) or formula (II) or compounds in patent WO2006/066080 are metabolized into their active forms which are useful TLR7 agonists.

As used herein, "hepatitis B virus" or "HBV" refers to a member of the Hepadnaviridae family having a small double-stranded DNA genome of approximately 3,200 base pairs and a tropism for liver cells. "HBV" includes hepatitis B virus that infects any of a variety of mammalian (e.g., human, non-human primate, etc.) and avian (duck, etc.) hosts. "HBV" includes any known HBV genotype, e.g., serotype A, B, C, D, E, F, and G; any HBV serotype or HBV subtype; any HBV isolate; HBV variants, e.g., HBeAg-negative variants, drug-resistant HBV variants (e.g., lamivudine-resistant variants; adefovir-resistant mutants; tenofovir-resistant mutants; entecavir-resistant mutants; etc.); and the like.

As used herein, "HBV capsid assembly inhibitor" refers to a compound that inhibits and/or disrupt and/or accelerates and/or hinders and/or delays and or reduces and/or modifies normal HBV capsid assembly (e.g., during maturation) and/or normal capsid disassembly (e.g., during infectivity) and/or perturbs capsid stability, thereby inducing aberrant capsid morphology and function.

In one embodiment of present invention, the HBV capsid assembly inhibitor is a compound of formula (III):

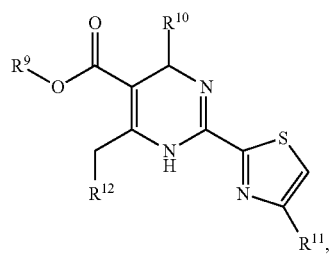

(III)

wherein $R^9$ is $C_{1-6}$alkyl;

$R^{10}$ is phenyl, which is once or twice or three times substituted by halogen or $C_{1-6}$alkyl;

$R^{11}$ is hydrogen or $C_{1-6}$alkyl;

$R^{12}$ is monocyclic, bicyclic fused or bicyclic bridged heterocyclyl;

or pharmaceutically acceptable salt, enantiomer or diastereomer thereof.

More particularly the HBV capsid assembly inhibitor according to present invention relates to 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid (disclosed in patent WO 2014/184328); or (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; or pharmaceutically acceptable salt, enantiomer or diastereomer thereof. In another embodiment, an "HBV capsid assembly inhibitor" more particularly is anyone of the compounds disclosed in patent WO2015/132276, WO 2014/184328 and WO2014/037480.

In one embodiment of present invention, the pharmaceutical composition comprises a TLR7 agonist and an HBV capsid assembly inhibitor, wherein TLR7 agonist and HBV capsid assembly inhibitor are independently selected from Table 1: (Compound 2 and 4 were disclosed in patent WO2015/132276; Compound 5 and 6 were disclosed in patent WO2014/184328; Compound 7, 8 and 9 were disclosed in patent WO2006/066080; Compound 10 was disclosed in patent WO2014/037480).

TABLE 1

List of TLR7 agonist and HBV capsid

| Entry | Class | Compound Name | Structure |
|---|---|---|---|
| Compound 1 | TLR7 agonist | [(1S)-1-[(2S,4R,5R)-5-(5-amino-2-oxo-thiazolo[4,5-d]pyrimidin-3-yl)-4-hydroxy-tetrahydrofuran-2-yl]propyl] acetate | 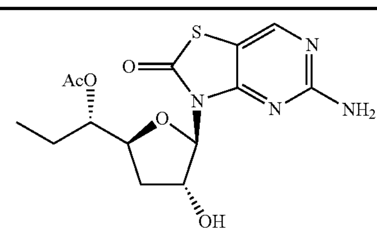 |

TABLE 1-continued

List of TLR7 agonist and HBV capsid

| Entry | Class | Compound Name | Structure |
|---|---|---|---|
| Compound 2 | HBV capsid inhibitor | 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 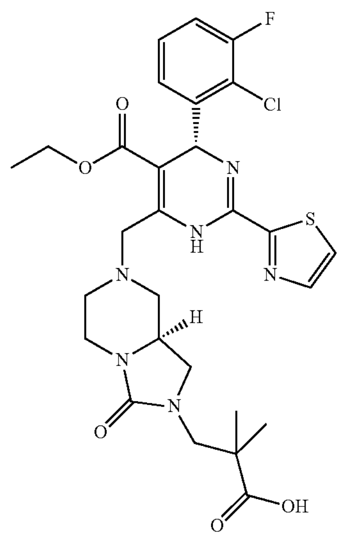 [SMILES: CCOC(=O)C1=C(CN2CCN3C(=O)N(CC(C)(C)C(=O)O)C[C@@H]3C2)NC(c2nccs2)=N[C@H]1c1cccc(F)c1Cl] |
| Compound 3 | TLR7 agonist | [(S)-[(2S,5R)-5-(5-amino-2-oxo-thiazolo[4,5-d]pyrimidin-3-yl)-1,3-oxathiolan-2-yl]-cyclopropyl-methyl]acetate | 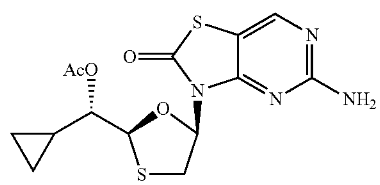 [SMILES: CC(=O)O[C@@H](C1CC1)[C@H]1O[C@@H](n2c(=O)sc3cnc(N)nc32)CS1] |
| Compound 4 | HBV capsid inhibitor | 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 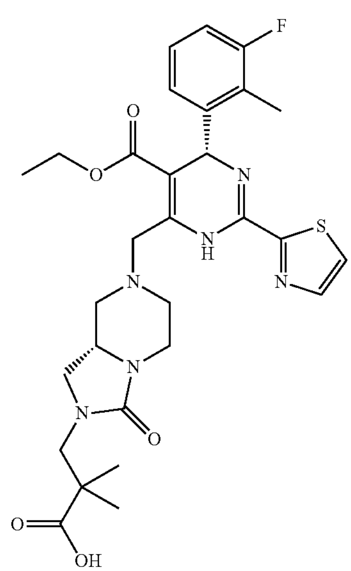 [SMILES: CCOC(=O)C1=C(CN2CCN3C(=O)N(CC(C)(C)C(=O)O)C[C@@H]3C2)NC(c2nccs2)=N[C@H]1c1cccc(F)c1C] |

TABLE 1-continued

List of TLR7 agonist and HBV capsid

| Entry | Class | Compound Name | Structure |
|---|---|---|---|
| Compound 5 | HBV capsid inhibitor | 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid | 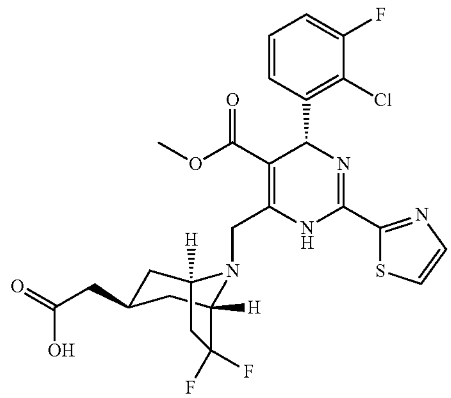 [SMILES: COC(=O)C1=C(CN2[C@@H]3C[C@H](CC(=O)O)C[C@H]2C(F)(F)C3)NC(c2nccs2)=N[C@H]1c1cccc(F)c1Cl] |
| Compound 6 | HBV capsid inhibitor | 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid | 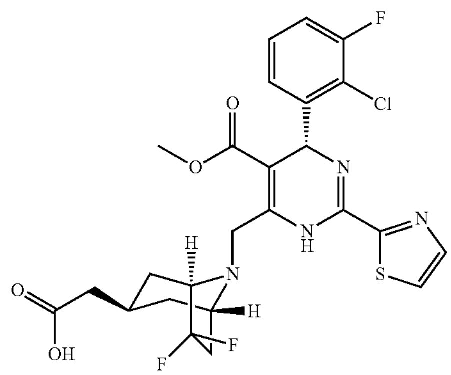 [SMILES: COC(=O)C1=C(CN2[C@H]3C[C@@H](CC(=O)O)C[C@@H]2C(F)(F)C3)NC(c2nccs2)=N[C@H]1c1cccc(F)c1Cl] |
| Compound 7 | TLR7 agonist | 5-amino-3-(3'-deoxy-β-D-ribofuranosyl)-3H-thiazolo[4,5-d]pyrimidin-2-one | 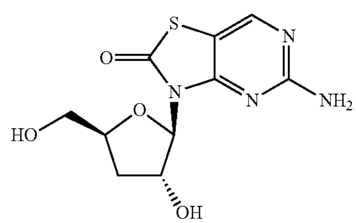 [SMILES: Nc1ncc2sc(=O)n([C@@H]3O[C@H](CO)C[C@H]3O)c2n1] |
| Compound 8 | TLR7 agonist | 5-amino-3-(2'-O-acetyl-3'-deoxy-β-D-ribofuranosyl)-3H-thiazolo[4,5-d]pyrimidin-2-one | 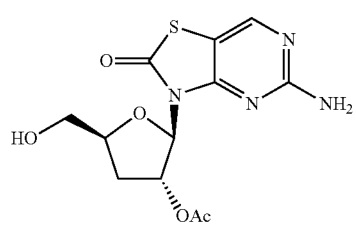 [SMILES: CC(=O)O[C@@H]1C[C@@H](CO)O[C@H]1n1c(=O)sc2cnc(N)nc21] |
| Compound 9 | TLR7 agonist | 5-amino-3-(3'-deoxy-β-D-ribofuranosyl)-3H,6H-thiazolo[4,5-d]pyrimidin-2,7-dione | 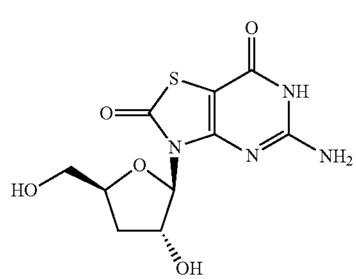 [SMILES: Nc1nc2c(sc(=O)n2[C@@H]2O[C@H](CO)C[C@H]2O)c(=O)[nH]1] |

TABLE 1-continued

List of TLR7 agonist and HBV capsid

| Entry | Class | Compound Name | Structure |
|---|---|---|---|
| Compound 10 | HBV capsid inhibitor | (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid | 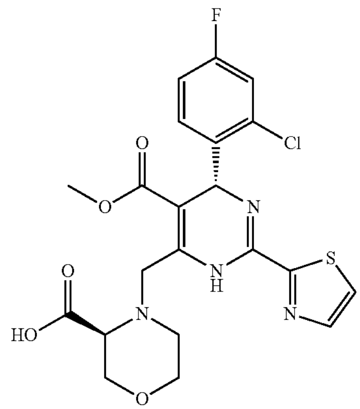 [SMILES: COC(=O)C1=C(CN2CCOC[C@H]2C(=O)O)NC(c2nccs2)=N[C@H]1c1ccc(F)cc1Cl] |
| Compound 11 | TLR7 agonist | [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl]acetate | 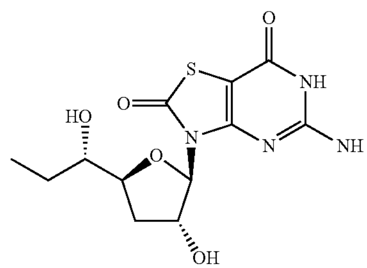 [SMILES: CC[C@H](O)[C@@H]1C[C@@H](O)[C@H](n2c(=O)sc3c(=O)[nH]c(N)nc32)O1] |

More particularly, the present invention relates to a pharmaceutical composition comprising a TLR7 agonist and an HBV capsid assembly inhibitor which is selected from any one of the following combinations:

Compound 1 and Compound 2; Compound 1 and Compound 4;
Compound 1 and Compound 5; Compound 1 and Compound 6;
Compound 1 and Compound 10; Compound 3 and Compound 2;
Compound 3 and Compound 4; Compound 3 and Compound 5;
Compound 3 and Compound 6; Compound 3 and Compound 10;
Compound 7 and Compound 2; Compound 7 and Compound 4;
Compound 7 and Compound 5; Compound 7 and Compound 6;
Compound 7 and Compound 10; Compound 8 and Compound 2;
Compound 8 and Compound 4; Compound 8 and Compound 5;
Compound 8 and Compound 6; Compound 8 and Compound 10;
Compound 9 and Compound 2; Compound 9 and Compound 4;
Compound 9 and Compound 5; Compound 9 and Compound 6;
Compound 9 and Compound 10; Compound 11 and Compound 2;
Compound 11 and Compound 4; Compound 11 and Compound 5;
Compound 11 and Compound 6; and Compound 11 and Compound 10.

The Compound 1 to 11 of the above said combination can be replaced by its corresponding pharmaceutically acceptable salt, enantiomer or diastereomer, which is another aspect of this invention.

The Compound 1 of the above said combination can be replaced by its corresponding mono, double or triple prodrugs, such as:

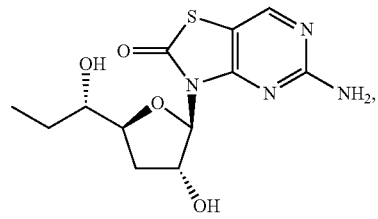

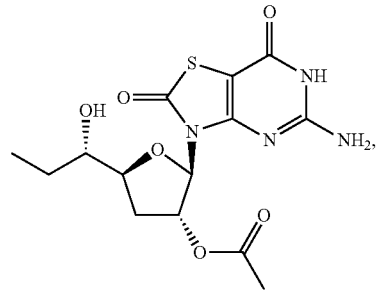

and their pharmaceutically acceptable salt, enantiomer or diastereomer.

In one embodiment of present invention, the pharmaceutical composition consists of a TLR7 agonist and an HBV capsid assembly inhibitor, in a pharmaceutically acceptable carrier. More particularly, the composition consists of:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2 S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2 S,4R,5R)-5-(5-amino-2-oxo-thiazolo[4,5-d]pyrimidin-3-yl)-4-hydroxy-tetrahydrofuran-2-yl]propyl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H-thiazolo[4,5-d]pyrimidin-2-one and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H,6H-thiazolo[4,5-d]pyrimidin-2,7-dione and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H-thiazolo[4,5-d]pyrimidin-2-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dim ethyl-propanoic acid;

5-amino-3-(3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dim ethyl-propanoic acid;

5-amino-3-(3'-deoxy-β-D-ribofuranosyl)-3H-thiazolo[4,5-d]pyrimidin-2-one and 2-[(1R,3S,5S)-8-[[(4R)-4-(2-chloro-3-fluoro-phenyl)-5-methoxycarbonyl-2-thiazol-2- yl-1,4-dihydropyrimidin-6-yl]methyl]-6,6-difluoro-8-azabicyclo[3.2.1]octan-3-yl]acetic acid;

5-amino-3-(3'-deoxy-β-D-ribofuranosyl)-3H-thiazolo[4,5-d]pyrimidin-2-one and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(2'-O-acetyl-3'-deoxy-β-D-ribofuranosyl)-3H-thiazolo[4,5-d]pyrimidin-2-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(2'-O-acetyl-3'-deoxy-β-D-ribofuranosyl)-3H-thiazolo[4,5-d]pyrimidin-2-one and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(2'-O-acetyl-3'-deoxy-β-D-ribofuranosyl)-3H-thiazolo[4,5-d]pyrimidin-2-one and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(3'-deoxy-β-D-ribofuranosyl)-3H,6H-thiazolo[4,5-d]pyrimidin-2,7-dione and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H,6H-thiazolo[4,5-d]pyrimidin-2,7-dione and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H,6H-thiazolo[4,5-d]pyrimidin-2,7-dione and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or 5-amino-3-(3'-deoxy-β-D-ribofuranosyl)-3H,6H-thiazolo[4,5-d]pyrimidin-2,7-dione and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; in a pharmaceutically acceptable carrier.

In another embodiment of present invention, the pharmaceutical composition consists of a TLR7 agonist and an HBV capsid assembly inhibitor, in a pharmaceutically acceptable carrier, most particularly, the composition consists of:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(2'-O-acetyl-3'-deoxy-β-D-ribofuranosyl)-3H-thiazolo[4,5-d]pyrimidin-2-one and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(2R,3R,5 S)-5-[(1S)-1-acetoxypropyl]-2-(5-amino-2,7-dioxo-6H-thiazolo[4,5-d]pyrimidin-3-yl)tetrahydrofuran-3-yl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(2R,3R,5 S)-5-[(1S)-1-acetoxypropyl]-2-(5-amino-2,7-dioxo-6H-thiazolo[4,5-d]pyrimidin-3-yl)tetrahydrofuran-3-yl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-di fluoro-8-azabicyclo[3.2.1]octan-3-yl]acetic acid; or

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; in a pharmaceutically acceptable carrier.

In another embodiment of present invention, other TLR7 agonists or HBV capsid assembly inhibitors can also be used in the pharmaceutical composition including small molecules or large molecules. Examples of other TLR7 agonists include, but not limited to, Imiquimod, Resiquimod, PF-4878691, SM-276001, ANA975, ANA773 and GS9620. Examples of other HBV capsid assembly inhibitors include, but not limited to, Bay 41-4109, Bay 38-7690, Bay 39-5493, GLS4, AT-61 and AT-130.

In another embodiment of present invention, the pharmaceutical composition can additionally comprise one or more other antiviral agents, which include, but not limited to, lamivudine, adefovir, tenofovir, telbivudine and entecavir.

Typical dosages of a TLR7 agonist and/or an HBV capsid assembly inhibitor can be in the ranges recommended by the manufacturer, and where indicated by in vitro responses in an animal models, can be reduced by up to about one order of magnitude concentration or amount. Thus, the actual dosage will depend upon the judgment of the physician, the condition of the patient, and the effectiveness of the therapeutic method based on the in vitro responsiveness of the appropriate animal models.

Another embodiment of present invention relates to a method for manufacturing a medicament for treatment or prophylaxis of hepatitis B virus infection, characterized in that a TLR7 agonist and an HBV capsid assembly inhibitor are used in the medicament.

A further embodiment of present invention relates to the method for manufacturing a medicament for treatment or prophylaxis of hepatitis B virus infection, characterized in that the TLR7 agonist and the HBV capsid assembly inhibitor are co-administered in the same formulation or different formulation.

For purposes of the present invention, "co-administer" refers to any administration of the TLR7 agonist and the HBV capsid assembly inhibitor as the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. Also, the two active agents can be administered either at the same time, or sequentially.

The TLR7 agonist and the HBV capsid assembly inhibitor can be administered with various pharmaceutically acceptable inert carriers in the form of tablets, capsules, lozengens, troches, hard candies, powders, sprays, creams, salves, suppositories, jellies, gels, pastes, lotions, ointments, elixirs, syrups, and the like. Administration of such dosage forms can be carried out in single or multiple doses. Carries include solid diluents of fillers, sterile aqueous media and various non-toxic organic solvents. Administration of such dosage forms can be carried out through, but not limited to, oral administration, parenteral administration, veterinary administration.

A further embodiment of present invention relates to the method for manufacturing a medicament for treatment or prophylaxis of hepatitis B virus infection, characterized in that the TLR7 agonist and the HBV capsid assembly inhibitor are intended for administration to a subject by the same route or different routes.

A further embodiment of present invention relates to the method for manufacturing a medicament for treatment or prophylaxis of hepatitis B virus infection, characterized in that the TLR7 agonist and the HBV capsid assembly inhibitor are intended for administration to a subject by parenteral or oral administration.

A further embodiment of present invention relates to the method for manufacturing a medicament for treatment or prophylaxis of hepatitis B virus infection, characterized in that the administration of TLR7 agonist and the HBV capsid assembly inhibitor to a subject is simultaneous or sequential.

In any of the methods of the present invention, the administration of agents simultaneously can be performed by separately or sequentially administering agents at the same time, or together as a fixed combination. Also, in any of the methods of the present invention, the administration of agents separately or sequentially can be in any order.

Another embodiment of present invention relates to the method for manufacturing a medicament for treatment or prophylaxis of hepatitis B virus infection, characterized in that TLR7 agonist thereof is a compound of formula (I) or formula (II), or pharmaceutically acceptable salt, enantiomer or diastereomer thereof. Particularly, the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate; [(S)-[(2S,5R)-5-(5-amino-2-oxo-thiazolo[4,5-d]pyrimidin-3-yl)-1,3-oxathiolan-2-yl]-cyclopropyl-methyl] acetate; 5-amino-3-(3'-deoxy-β-D-ribofuranosyl)-3H-thiazolo[4,5-d]pyrimidin-2-one; 5-amino-3-(2'-O-acetyl-3'-deoxy-β-D-ribofuranosyl)-3H-thiazolo[4,5-d]pyrimidin-2-one; 5-amino-3-(3'-deoxy-β-D-ribofuranosyl)-3H,6H-thiazolo[4,5-d]pyrimidin-2,7-dione; or [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate; or pharmaceutically acceptable salt, enantiomer or diastereomer thereof.

Another embodiment of present invention relates to the method for manufacturing a medicament for treatment or prophylaxis of hepatitis B virus infection, characterized in that the HBV capsid assembly inhibitor thereof is a compound of formula (III), or pharmaceutically acceptable salt, enantiomer or diastereomer thereof. Particularly, the HBV capsid assembly inhibitor is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid;

or (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

or pharmaceutically acceptable salt, enantiomer or diastereomer thereof.

Another embodiment of present invention relates to the method for manufacturing a medicament for treatment or prophylaxis of hepatitis B virus infection, characterized in that the medicament additionally comprising one or more other antiviral agents, which include, but not limited to, lamivudine, adefovir, tenofovir, telbivudine and entecavir.

Another embodiment of present invention relates to the method for manufacturing a medicament for treatment or prophylaxis of hepatitis B virus infection, wherein the TLR7 agonist and the HBV capsid assembly inhibitor used in the medicament are:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydro-pyrimidin-6-yl]methyl]-6,6-difluoro-8-azabicyclo[3.2.1]octan-3-yl]acetic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and 3-[(8aS)-7-[[(4 S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 5-amino-3-(2'-O-acetyl-3'-deoxy-β-D-ribofuranosyl)-3H-thiazolo[4,5-d]pyrimidin-2-one and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; in a pharmaceutically acceptable carrier.

Another embodiment of present invention relates to a kit comprising a container comprising a TLR7 agonist and an HBV capsid assembly inhibitor, said kit can further comprise a sterile diluent.

A further embodiment of present invention relates to the said kit, wherein the kit can further comprise a package insert comprising printed instructions directing the use of a combined treatment of a TLR7 agonist and an HBV capsid assembly inhibitor as a method for treatment or prophylaxis of hepatitis B virus infection.

Another embodiment of present invention relates to the said kit, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate; [(S)-[(2S,5R)-5-(5-amino-2-oxo-thiazolo[4,5-d]pyrimidin-3-yl)-1,3-oxathiolan-2-yl]-cyclopropyl-methyl] acetate; 5-amino-3-(3'-deoxy-β-D-ribofuranosyl)-3H-thiazolo[4,5-d]pyrimidin-2-one; 5-amino-3-(2'-O-acetyl-3'-deoxy-β-D-ribofuranosyl)-3H-thiazolo[4,5-d]pyrimidin-2-one; 5-amino-3-(3'-deoxy-β-D-ribofuranosyl)-3H,6H-thiazolo[4,5-d]pyrimidin-2,7-dione; or [(2R,3R,5S)-5-[(1S)-1-acetoxy-propyl]-2-(5-amino-2,7-dioxo-6H-thiazolo[4,5-d]pyrimidin-3-yl)tetrahydrofuran-3-yl] acetate; or pharmaceutically acceptable salt, enantiomer or diastereomer thereof; and/or the HBV capsid assembly inhibitor is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; or pharmaceutically acceptable salt, enantiomer or diastereomer thereof.

Another embodiment of present invention relates to the said kit, wherein the TLR7 agonist and the HBV capsid assembly inhibitor used in the container are:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2 S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4 S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2 S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 5-amino-3-(2'-O-acetyl-3'-deoxy-β-D-ribofuranosyl)-3H-thiazolo[4,5-d]pyrimidin-2-one and (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; in a pharmaceutically acceptable carrier.

Another embodiment of present invention relates to a method for the treatment or prophylaxis of hepatitis B virus infection, comprising administration to a subject with an effective first amount of a TLR7 agonist, or pharmaceutically acceptable salt, enantiomer or diastereomer thereof; and a second amount of HBV capsid assembly inhibitor, or pharmaceutically acceptable salt, enantiomer or diastereomer thereof; wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate; [(S)-[(2S,5R)-5-(5-amino-2-oxo-thiazolo[4,5-d]pyrimidin-3-yl)-1,3- oxathiolan-2-yl]-cyclopropyl-methyl] acetate; 5-amino-3-(3'-deoxy-β-D-ribofuranosyl)-3H-thiazolo[4,5-d]pyrimidin-2-one; 5-amino-3-(2'-O-acetyl-3'-deoxy-β-D-ribofuranosyl)-3H-thiazolo[4,5-d]pyrimidin-2-one; 5-amino-3-(3'-deoxy-β-D-ribofuranosyl)-3H,6H-thiazolo[4,5-d]pyrimidin-2,7-dione; or [(2R,3R,5S)-5-[(1S)-1-acetoxy-propyl]-2-(5-amino-2,7-dioxo-6H-thiazolo[4,5-d]pyrimidin-3-yl)tetrahydrofuran-3-yl] acetate; or pharmaceutically acceptable salt, enantiomer or diastereomer thereof; and/or the HBV capsid assembly inhibitor is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; or pharmaceutically acceptable salt, enantiomer or diastereomer thereof.

Another embodiment of present invention relates to use of pharmaceutical composition herein mentioned above as an antiviral medicament, in particular as the medicament for treatment or prophylaxis of hepatitis B virus infection.

Another embodiment of present invention relates to the use of a TLR7 agonist and an HBV capsid assembly inhibitor for the manufacture of pharmaceutical composition herein mentioned above as an antiviral medicament, in particular the medicament for treatment or prophylaxis of hepatitis B virus infection.

EXAMPLES

The invention will be more fully understood by reference to the following examples. They should not, however, be construed as limiting the scope of the invention.

Example 1

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate (Compound 1)

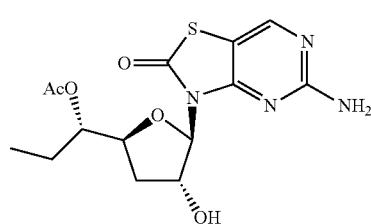

Compound 1 was prepared through the following scheme:

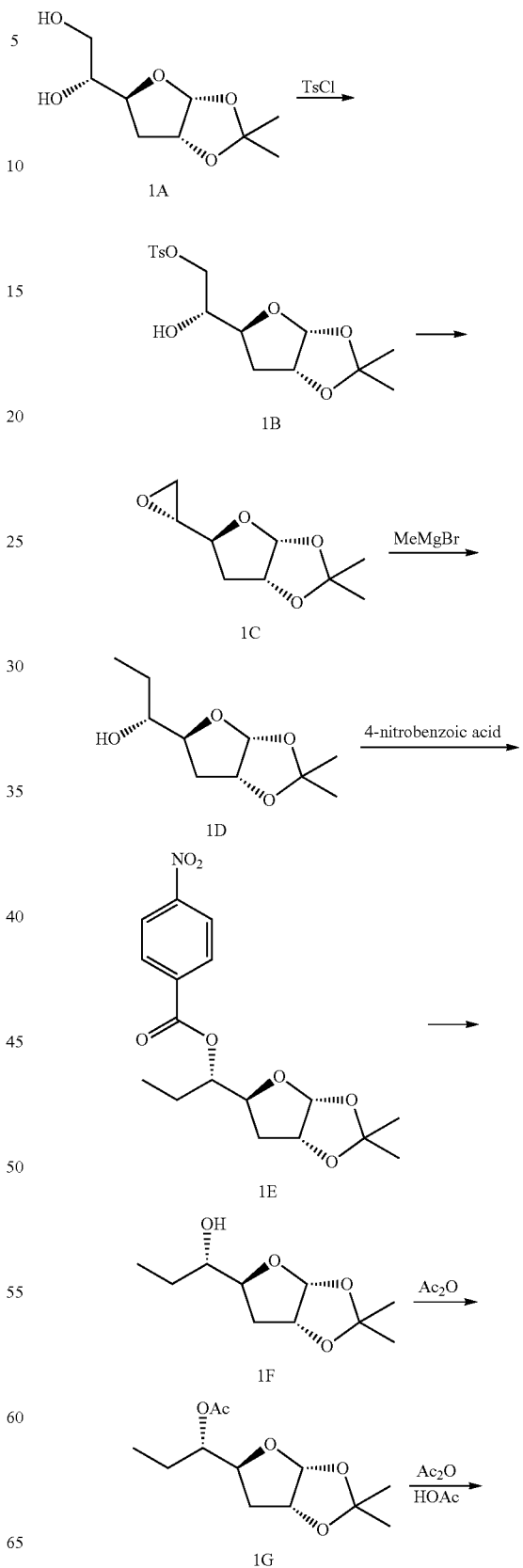

-continued

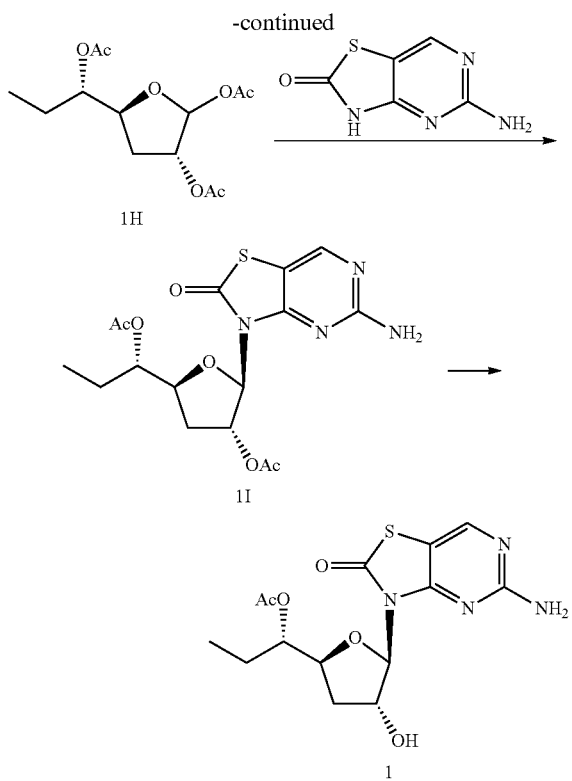

Preparation of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate

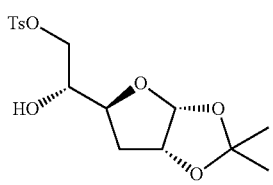

To a solution of (1R)-1-[(3aR,5S,6aR)-2,2-dimethyl-3a,5,6,6a-tetrahydrofuro[2,3-d][1,3]dioxol-5-yl]ethane-1,2-diol (compound 1A, 100 g, 490 mmol) in dry pyridine (1000 mL) was added p-toluenesulfonyl chloride (139 g, 735 mmol) at 0° C. After being stirred at room temperature for 12 hours, the resulted solution was quenched by water (100 mL) and concentrated in vacuo. The residue was purified by column chromatography on silica gel (eluting with 1:10 to 1:3 EtOAc in petroleum ether) to afford 130 g of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate (compound 1B) as a slight yellow oil.

Compound 1B:
$^1$H NMR (400 MHz, CDCl$_3$) δppm: 7.82 (d, J=8.00 Hz, 2H), 7.38 (d, J=8.00 Hz, 2H), 5.78 (d, J=3.76 Hz, 1H), 4.75 (t, J=4.00 Hz, 1H), 4.20-4.12 (m, 2H), 4.03-3.97 (m, 2H), 2.48 (s, 3H), 2.39 (d, J=3.51 Hz, 1H), 2.08-2.15 (m, 1H), 1.75-1.80 (m, 1H), 1.51 (s, 3H), 1.33 (s, 3H).

Preparation of (3aR,5S,6aR)-2,2-dimethyl-5-[(2R)-oxiran-2-yl]-3a,5,6,6a-tetrahydrofuro[2,3-d][1,3]dioxole

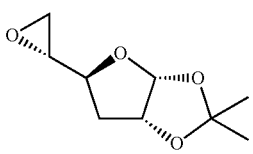

To a solution of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate (compound 1B, 100 g, 280 mmol) in anhydrous THF (1500 mL) cooled at −70° C. was added potassium bis(trimethylsilyl)amide (340 mL, 340 mmol, 1 M in THF) under N$_2$ atmosphere. After being stirred at −70° C. for 1 hour, the reaction mixture was poured into saturated NH$_4$Cl solution. The organic layer was separated and the aqueous phase was extracted with EtOAc. The combined organic layers were dried over Na$_2$SO$_4$ and concentrated in vacuo. The residue was purified by column chromatography on silica gel (eluting with 1:3 EtOAc in petroleum ether) to afford 40.5 g of (3aR,5S,6aR)-2,2-dimethyl-5-[(2R)-oxiran-2-yl]-3a,5,6,6a-tetrahydrofuro[2,3-d][1,3]dioxole (compound 1C) as a slight yellow oil.

Compound 1C:
$^1$H NMR: (400 MHz, CDCl$_3$) δppm: 5.87 (d, J=3.76 Hz, 1H), 4.77 (t, J=4.00, 1H), 4.20-4.28 (m, 1H), 3.14-3.20 (m, 1H), 2.83-2.88 (m, 1H), 2.63 (dd, J=5.00, 2.80 Hz, 1H), 2.09 (dd, J=12.00, 4.00 Hz, 1H), 1.69-1.79 (m, 1H), 1.52 (s, 3H), 1.34 (s, 3H).

Preparation of (1R)-1-[(3aR,5S,6aR)-2,2-dimethyl-3a,5,6,6a-tetrahydrofuro[2,3-d][1,3]dioxol-5-yl]propan-1-ol

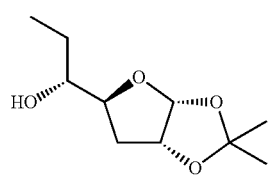

To a suspension of CuI (19.3 g, 107 mmol) in dry THF (2000 mL) under N$_2$ atmosphere was added methyl magnesium bromide (3 M in diethyl ether, 537 mL, 1.61 mol) at −70° C. After being stirred at the same temperature for 1 hour, a solution of (3aR,5S,6aR)-2,2-dimethyl-5-[(2R)-oxiran-2-yl]-3a,5,6,6a-tetrahydrofuro[2,3-d][1,3]dioxole (compound 1C, 100 g, 537 mmol, dissolved in anhydrous THF 200 mL) was added to reaction mixture dropwise. After being stirred at −70° C. for additional 2 hours, the reaction mixture was poured into saturated NH$_4$Cl solution. The organic layer was separated and the aqueous phase was extracted with EtOAc twice. The combined organic layers were dried over Na$_2$SO$_4$ and concentrated in vacuo. The residue was purified by column chromatography on silica gel (eluting with 1:3 EtOAc in petroleum ether) to afford 82 g of (1R)-1-[(3 aR,5S,6aR)-2,2-dimethyl-3a,5,6,6a-tetrahydrofuro[2,3-d][1,3]dioxol-5-yl]propan-1-ol (compound 1D) as a slight yellow solid.

Compound 1D:

$^1$H NMR (400 MHz, CDCl$_3$) δppm: 5.83 (d, J=3.76 Hz, 1H), 4.81-4.73 (m, 1H), 4.26-4.19 (m, 1H), 3.91-3.82 (m, 1H), 2.08-2.02 (m, 1H), 1.93-1.89 (m, 1H), 1.54 (s, 3H), 1.49-1.39 (m, 2H), 1.34 (s, 3H), 1.02 (t, J=7.53 Hz, 3H).

Preparation of [(1S)-1-[(3aR,5S,6aR)-2,2-dimethyl-3a,5,6,6a-tetrahydrofuro[2,3-d][1,3]dioxol-5-yl]propyl] 4-nitrobenzoate

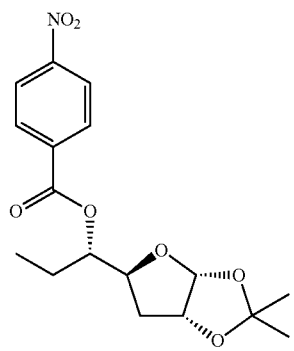

1E

To a stirred solution of (1R)-1-[(3 aR,5S,6aR)-2,2-dimethyl-3a,5,6,6a-tetrahydrofuro[2,3-d][1,3]dioxol-5-yl]propan-1-ol (compound 1D, 50 g, 245 mmol), triphenylphosphine (195 g, 743 mmol), 4-nitrobenzoic acid (124 g, 743 mmol) in THF (1200 mL) was added diethyl azodicarboxylate (130 g, 743 mmol) dropwise at 0° C. under N$_2$. After being stirred at 18° C. for 10 hours, the mixture was quenched by addition of saturated NaHCO$_3$ solution and extracted with EtOAc. The organic layers were combined, dried over Na$_2$SO$_4$ and concentrated in vacuo. The residue was purified by column chromatography on silica gel (eluting with 1:3 EtOAc in petroleum ether) to afford 61 g of [(1S)-1-[(3aR,5S,6aR)-2,2-dimethyl-3a,5,6,6a-tetrahydrofuro[2,3-d][1,3]dioxol-5-yl]propyl] 4-nitrobenzoate (compound 1E) as a slight yellow solid.

Compound 1E:

$^1$H NMR (400 MHz, CDCl$_3$) δppm: 8.34-8.22 (m, 4H), 5.85 (d, J=3.76 Hz, 1H), 5.23-5.17 (m, 1H), 4.76 (t, J=4.27 Hz, 1H), 4.48-4.39 (m, 1H), 2.12 (dd, J=13.30, 4.52 Hz, 1H), 1.88-1.78 (m, 2H), 1.71-1.62 (m, 1H), 1.55 (s, 3H), 1.34 (s, 3H), 1.01 (t, J=7.40 Hz, 3H).

Preparation of (1S)-1-[(3aR,5S,6aR)-2,2-dimethyl-3a,5,6,6a-tetrahydrofuro[2,3-d][1,3]dioxol-5-yl]propan-1-ol

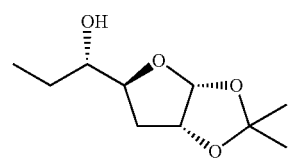

1F

To a solution of [(1S)-1-[(3aR,5S,6aR)-2,2-dimethyl-3a,5,6,6a-tetrahydrofuro[2,3-d][1,3]dioxol-5-yl]propyl] 4-nitrobenzoate (compound 1E, 100 g, 285 mmol) in methanol (1200 mL) was added K$_2$CO$_3$ (78.7 g, 570 mmol). After being stirred at room temperature for 10 minutes, the resulted mixture was filtered. The filtrate was concentrated in vacuo. The residue was purified by column chromatography on silica gel (eluting with 1:8 EtOAc in petroleum ether) to afford 54.7 g of (1S)-1-[(3aR,5S,6aR)-2,2-dimethyl-3a,5,6,6a-tetrahydrofuro[2,3-d][1,3]dioxol-5-yl]propan-1-ol (compound 1F) as a slight yellow solid.

Compound 1F:

$^1$H NMR (400 MHz, CDCl$_3$) δppm: 5.81 (d, J=3.64 Hz, 1H), 4.75 (t, J=4.20 Hz, 1H), 4.18-4.11 (m, 1H), 3.49-3.40 (m, 1H), 2.07-2.00 (m, 2H), 1.84-1.75 (m, 1H), 1.59-1.47 (m, 5H), 1.32 (s, 3H), 1.01 (t, J=7.40 Hz, 3H).

Preparation of [(1S)-1-[(3aR,5S,6aR)-2,2-dimethyl-3a,5,6,6a-tetrahydrofuro[2,3-d][1,3]dioxol-5-yl]propyl] acetate

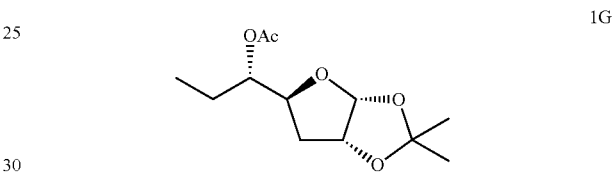

1G

To a stirred solution of (1S)-1-[(3aR,5S,6aR)-2,2-dimethyl-3a,5,6,6a-tetrahydrofuro[2,3-d][1,3]dioxol-5-yl]propan-1-ol (compound 1F, 13.5 g, 67 mmol), TEA (81 g, 804 mmol), DMAP (1.6 g, 13 mmol) in anhydrous DCM (150 mL) was added acetic anhydride (62 g, 603 mmol). After being stirred at 22° C. for 10 hours, the reaction was quenched by the saturated NaHCO$_3$ solution. The organic layer was separated and the aqueous phase was extracted with EtOAc. The combined organic layers were dried over Na$_2$SO$_4$, and concentrated in vacuo. The residue was purified by column chromatography on silica gel (eluting with 1:8 EtOAc in petroleum ether) to afford 13 g of [(1S)-1-[(3aR,5S,6aR)-2,2-dimethyl-3a,5,6,6a-tetrahydrofuro[2,3-d][1,3]dioxol-5-yl]propyl] acetate (compound 1G) as a colourless oil.

Compound 1G:

$^1$H NMR (400 MHz, CDCl$_3$) δppm: 5.83 (d, J=3.76 Hz, 1H), 4.92 (dt, J=7.97, 5.18 Hz, 1H), 4.74 (t, J=4.00 Hz, 1H), 4.35-4.27 (m, 1H), 2.12 (s, 3H), 2.08-1.99 (m, 1H), 1.74-1.56 (m, 3H), 1.53 (s, 3H), 1.34 (s, 3H), 0.95 (t, J=7.40 Hz, 3H).

Preparation of [(3R,5S)-2-acetoxy-5-[(1S)-1-acetoxypropyl]tetrahydrofuran-3-yl] acetate

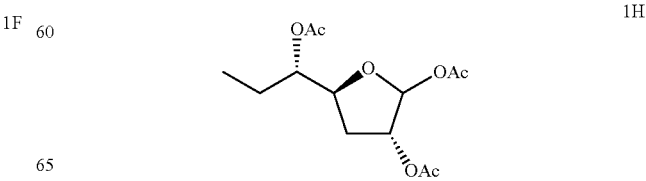

1H

To a solution of [(1S)-1-[(3aR,5S,6aR)-2,2-dimethyl-3a,5,6,6a-tetrahydrofuro[2,3-d][1,3]dioxol-5-yl]propyl] acetate (compound 1G, 4.8 g, 20 mmol), acetic acid (12.2 g, 200 mmol) and acetic anhydride (10.2 g, 100 mmol) in anhydrous DCM (100 mL) was added concentrated $H_2SO_4$ (0.5 mL) at 0° C. After being stirred at 22° C. for 3 hours, the reaction was quenched by addition of saturated $NaHCO_3$ solution. The organic layer was separated and the aqueous phase was extracted with EtOAc. The combined organic layers were dried over $Na_2SO_4$, filtered, and concentrated in vacuo. The residue was purified by column on silica gel (eluting with 1:8 EtOAc in petroleum ether) to afford 2.3 g of [(3R,5S)-2-acetoxy-5-[(1S)-1-acetoxypropyl]tetrahydrofuran-3-yl] acetate (compound 1H) as a colourless oil.

Compound 1H:
$^1$H NMR (400 MHz, $CDCl_3$) δppm: 6.12 (s, 1H), 5.19 (d, J=4.52 Hz, 1H), 4.83-4.91 (m, 1H), 4.34-4.44 (m, 1H), 2.09-2.19 (m, 9H), 1.51-1.74 (m, 4H), 0.94 (t, J=7.40 Hz, 3H).

Preparation of [(2R,3R,5S)-5[(1S)-1-acetoxypropyl]-2-(5-amino-2-oxo-thiazolo[4,5-d]pyrimidin-3-yl)tetrahydrofuran-3-yl] acetate

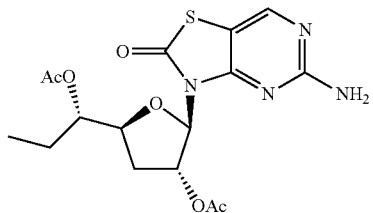

1I

To a suspension of 5-amino-3H-thiazolo[4,5-d]pyrimidin-2-one (3.5 g, 20.8 mmol) in xylene (160 mL) was added BSA (21.2 g, 104 mmol). The reaction mixture was stirred at 70° C. for 1 hour under argon to form a clear solution. After some of xylene and excrescent BSA were evaporated, [(3R,5S)-2-acetoxy-5-[(1S)-1-acetoxypropyl]tetrahydrofuran-3-yl] acetate (compound 1H, 3.0 g, 10.4 mmol) and TMSOTf (2.6 g, 11.6 mmol) were added in sequence at 0° C. After being heated with stirring at 65° C. for 2 hours, the reaction was quenched with water (30 mL), extracted with EA (30 mL) three times. The combined organic layers were dried over $Na_2SO_4$ and concentrated in vacuo. The residue was purified by column on silica gel (eluting with 1:10 to 1:1 EtOAc in petroleum ether) to give 2.0 g of [(2R,3R,5S)-5-[(1S)-1-acetoxypropyl]-2-(5-amino-2-oxo-thiazolo[4,5-d]pyrimidin-3-yl)tetrahydrofuran-3-yl] acetate (compound 1I) as a white solid.

Compound 1I:
$^1$H NMR (400 MHz, $CDCl_3$) δppm: 8.15 (s, 1H), 6.04 (d, J=1.51 Hz, 1H), 5.80 (d, J=7.03 Hz, 1H), 5.27 (br. s., 2H), 4.98-5.04 (m, 1H), 4.32-4.39 (m, 1H), 2.63-2.77 (m, 1H), 2.13 (s, 3H), 2.09 (s, 3H), 2.00-2.07 (m, 1H), 1.61-1.75 (m, 2H), 0.94 (t, J=7.40 Hz, 3H).

Preparation of [(1S)-1-[(2S,4R,5R)-5-(5-amino-2-oxo-thiazolo[4,5-d]pyrimidin-3-yl)-4-hydroxy-tetrahydrofuran-2-yl]propyl] acetate

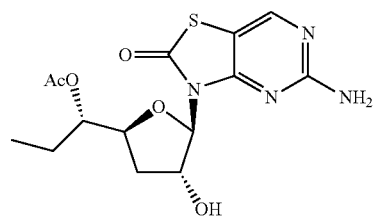

1

[(2R,3R,5S)-5-[(1S)-1-acetoxypropyl]-2-(5-amino-2-oxo-thiazolo[4,5-d]pyrimidin-3-yl)tetrahydrofuran-3-yl] acetate (compound 1I, 3.2 g, 8.0 mmol) and $K_2CO_3$ (2.2 g, 16.0 mmol) were suspended in anhydrous ethanol (85 mL) at room temperature. Methanol (85 mL) was added dropwise under $N_2$ atmosphere. After the addition, the mixture was stirred at room temperature for 10 minutes (monitored by TLC). After the reaction, the mixture was poured into saturate $NH_4Cl$, extracted with EA (150 mL) four times. The combined organic layers were dried over $Na_2SO_4$ concentrated in vacuo. The residue was purified by column on silica gel (eluting with 1:100 to 1:70 MeOH in DCM) to give the crude product, which was further purified by flash column (eluting with acetonitrile and water) to give 1.64 g of [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (Compound 1) as a white power.

Compound 1:
$^1$H NMR (400 MHz, Methanol-$d_4$) δppm: 8.19 (s, 1H), 6.02-6.05 (m, 1H), 4.94-5.00 (m, 2H), 4.33-4.40 (m, 1H), 2.58-2.68 (m, 1H), 2.03 (s, 3H), 1.86-1.96 (m, 1H), 1.56-1.77 (m, 2H), 0.93 (t, J=7.40 Hz, 3H). MS obsd. (ESI$^-$) [(M+H)$^+$]: 355.0.

Example 2

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

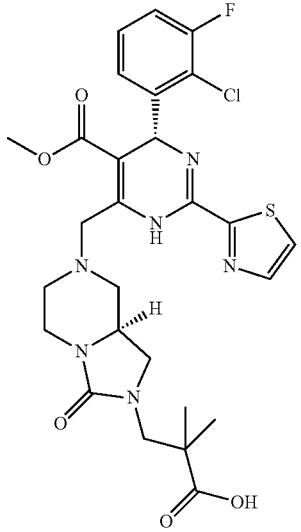 [SMILES: COC(=O)C1=C(CN2CCN3C(=O)N(CC(C)(C)C(=O)O)C[C@@H]3C2)NC(c2nccs2)=N[C@H]1c1cccc(F)c1Cl]

Compound 2 was prepared through following scheme:

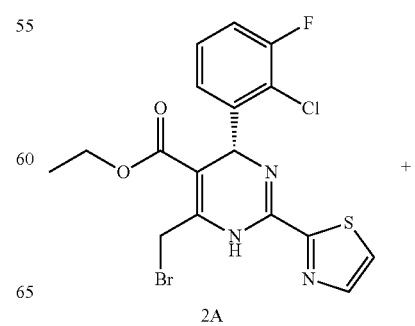

2A

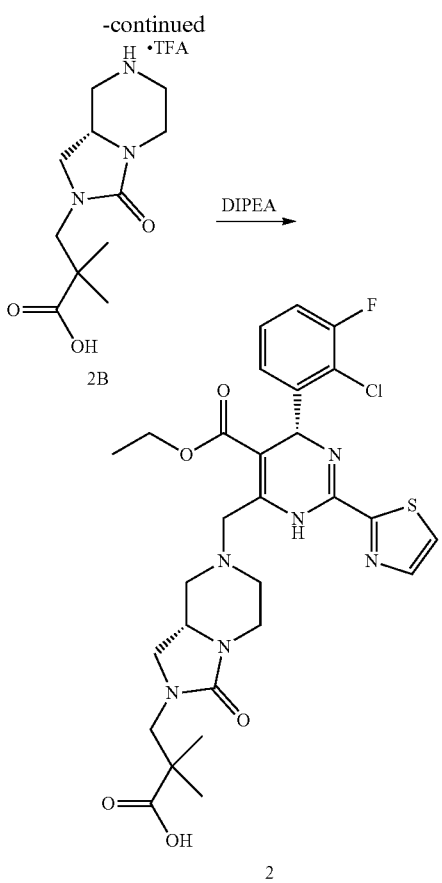

To a stirred solution of ethyl (4R)-6-(bromomethyl)-4-(2-chloro-3-fluoro-phenyl)-2-thiazol-2-yl-1,4-dihydropyrimidine-5-carboxylate (compound 2A, 0.073 g, 0.16 mmol) and 3-[(8aS)-3-oxo-1,5,6,7,8,8a-hexahydroimidazo[1,5-a]pyrazin-2-yl]-2,2-dimethyl-propanoic acid (compound 2B, crude, 0.25 mmol) in 1,2-dichloroethane (5 mL) was added dropwise DIPEA (0.078 mL, 0.45 mmol). The reaction mixture was stirred at room temperature until the disappearance of compound 2A. The mixture was then diluted with EtOAc (50 mL) and washed successively with saturated aqueous NH₄Cl solution and brine. The organic layer was separated and dried over Na₂SO₄. The solvent was removed in vacuo and the crude product was purified by prep-HPLC to give 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Compound 2) as a light yellow solid (12 mg). ¹H NMR (400 MHz, Methanol-d₄) ppm 7.92-8.02 (m, 1H), 7.70-7.80 (m, 1H), 7.21-7.36 (m, 2H), 7.10-7.21 (m, 1H), 6.19-6.28 (m, 1H), 3.99-4.14 (m, 3H), 3.81-3.96 (m, 3H), 3.47-3.56 (m, 1H), 3.38-3.44 (m, 1H), 3.27-3.32 (m, 1H), 3.15-3.25 (m, 1H), 3.07-3.14 (m, 1H), 2.79-2.96 (m, 2H), 2.30-2.41 (m, 1H), 2.13-2.23 (m, 1H), 1.20 (d, J=2.76 Hz, 6H), 1.13 (m, 3H). MS: calc'd 619 (M+H)⁺, measured 619 (M+H)⁺.

Preparation of ethyl (4R)-6-(bromomethyl)-4-(2-chloro-3-fluoro-phenyl)-2-thiazol-2-yl-1,4-dihydro-pyrimidine-5-carboxylate (compound 2A)

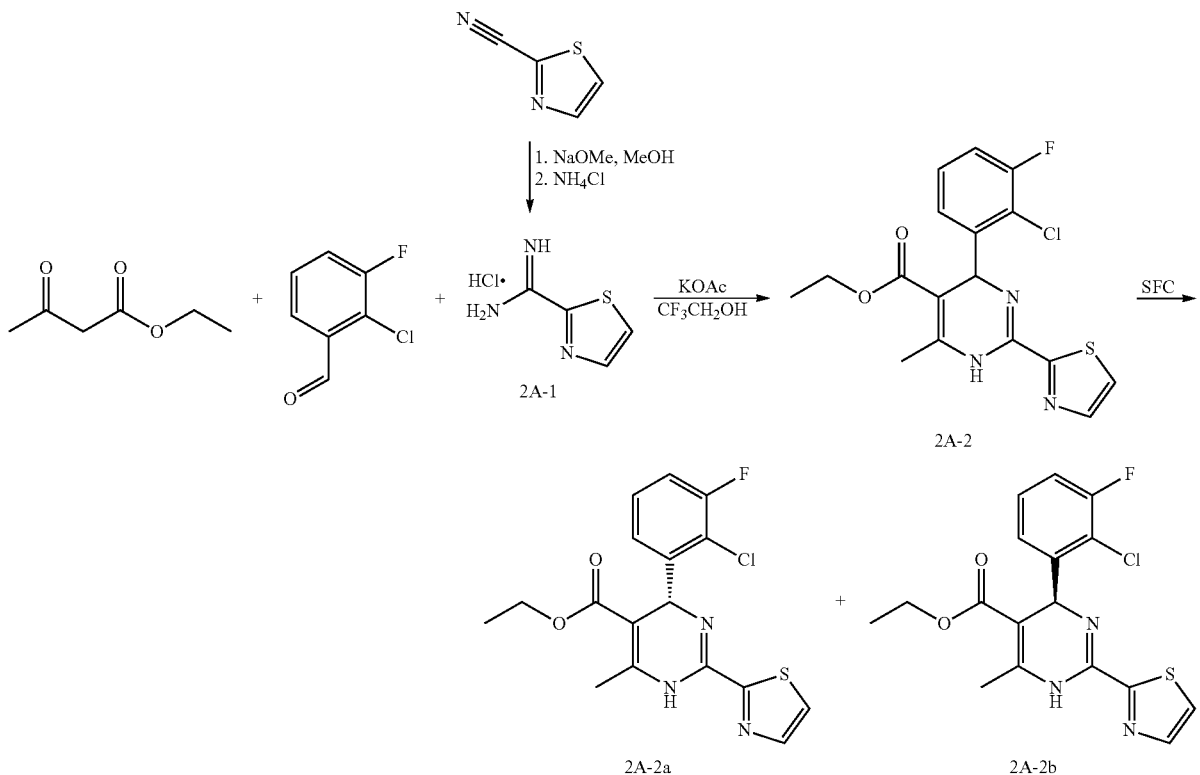

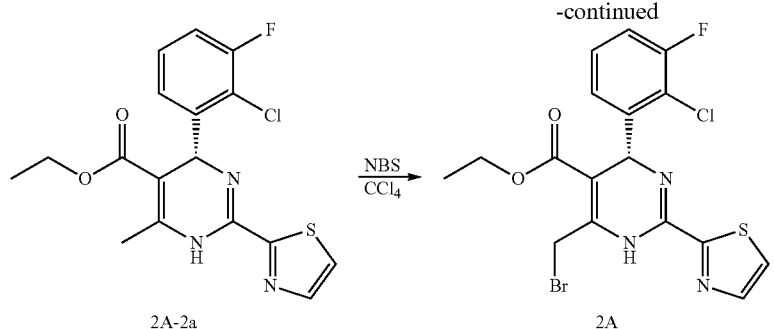

2A-2a → (NBS, CCl₄) → 2A

Preparation of thiazole-2-carboxamidine hydrochloride (compound 2A-1)

To a stirred solution of thiazole-2-carbonitrile (1.5 g, 14 mmol) in 5 mL of dry MeOH was added dropwise a solution of sodium methoxide (0.74 g, 14 mmol) in 10 mL of dry methanol. The reaction mixture was stirred at room temperature until the disappearance of starting material. Then ammonium chloride (1.5 g, 28 mmol) was added in one portion and the reaction mixture was stirred overnight. The undissolved material was removed by filtration and the filtrate was concentrated to afford thiazole-2-carboxamidine hydrochloride (compound 2A-1, 2.1 g) as a grey solid which was used directly in the next step without further purification. MS: calc'd 128 (M+H)⁺, measured 128 (M+H)⁺.

Preparation of ethyl 4-(2-chloro-3-fluoro-phenyl)-6-methyl-2-thiazol-2-yl-1,4-dihydropyrimidine-5-carboxylate (compound 2A-2)

To a stirred solution of thiazole-2-carboxamidine hydrochloride (1.3 g, 10 mmol), ethyl acetoacetate (1.3 g, 10 mmol) and 2-chloro-3-fluorobenzaldehyde (1.6 g, 10 mmol) in trifluoroethanol (30 mL) was added potassium acetate (2.0 g, 20 mmol). The reaction mixture was refluxed for 16 hours. After it was cooled to room temperature, the reaction mixture was concentrated and the residue was dissolved in ethyl acetate and then washed with brine. The organic layer was dried over Na₂SO₄. The solvent was removed in vacuo and the residue was purified by silica gel column chromatography (ethyl acetate/petroleum ether: from ¼ to ½) to afford ethyl 4-(2-chloro-3-fluoro-phenyl)-6-methyl-2-thiazol-2-yl-1,4-dihydropyrimidine-5-carboxylate (compound 2A-2, 2.8 g) as a yellow solid. MS: calc'd (M+H)⁺380, measured (M+H)⁺380.

Preparation of ethyl (4R)-4-(2-chloro-3-fluoro-phenyl)-6-methyl-2-thiazol-2-yl-1,4-dihydropyrimidine-5-carboxylate (compound 2A-2a)

Figure 2:
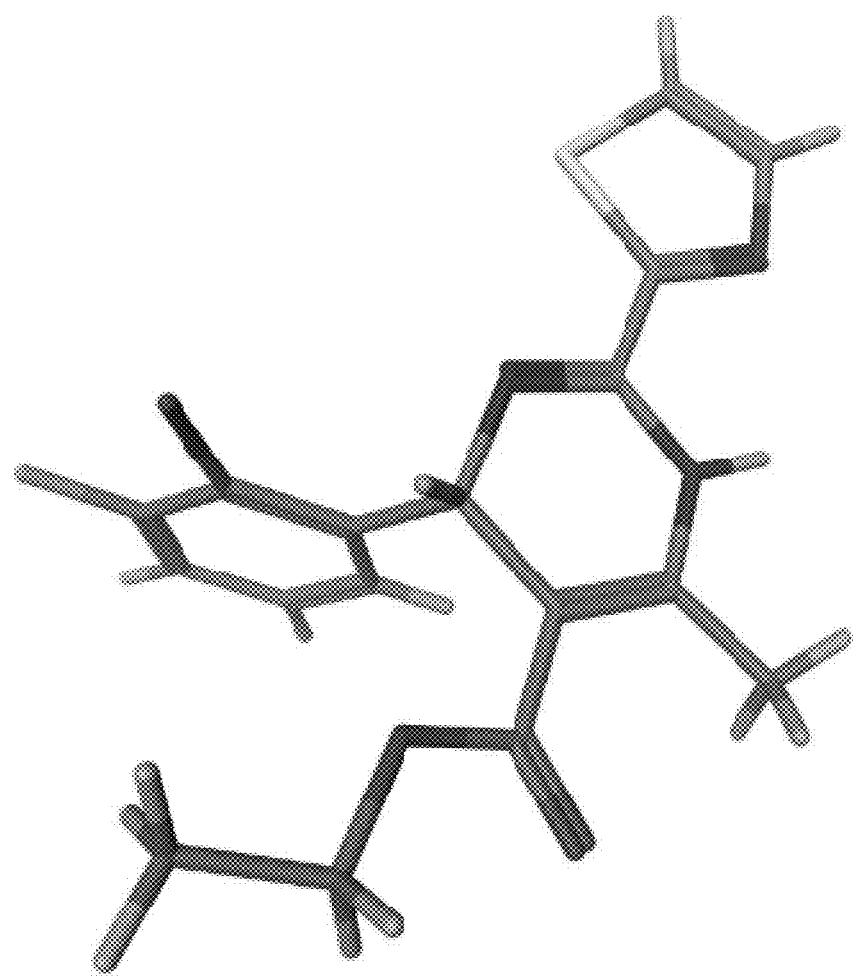

A chiral separation of racemic compound 2A-2 eluting with a mixed solvent of 85% supercritical CO₂/15% EtOH at 100 mL/min rate on SFC (SFC-Multigram; IC: 5×250 mm, gave two enantiomers of ethyl (4R)-4-(2-chloro-3-fluoro-phenyl)-6-methyl-2-thiazol-2-yl-1,4-dihydropyrimidine-5-carboxylate (compound 2A-2a, faster eluting) and ethyl (4S)-4-(2-chloro-3-fluoro-phenyl)-6-methyl-2-thiazol-2-yl-1,4-dihydropyrimidine-5-carboxylate (compound 2A-2b, slower eluting). The absolute configuration of desired (−)-enantiomer compound 2A-2a ([α]$_D^{20}$ −46.6 (c 0.28, MeOH)) was determined by X-ray diffraction study (FIG. 2).

Preparation of ethyl (4R)-6-(bromomethyl)-4-(2-chloro-3-fluoro-phenyl)-2-thiazol-2-yl-1,4-dihydropyrimidine-5-carboxylate (compound 2A)

To a stirred solution of ethyl (4R)-4-(2-chloro-3-fluoro-phenyl)-6-methyl-2-thiazol-2-yl-1,4-dihydropyrimidine-5-carboxylate (compound 2A-2a, 0.37 g, 1.0 mmol) in CCl₄ (5 mL) was added NBS (0.20 g, 1.1 mmol) in portions. After the reaction mixture was stirred at room temperature for 1 hour, the solvent was removed in vacuo and the residue was purified by silica gel column chromatography to give ethyl (4R)-6-(bromomethyl)-4-(2-chloro-3-fluoro-phenyl)-2-thiazol-2-yl-1,4-dihydropyrimidine-5-carboxylate (compound 2A, 0.35 g) as a yellow solid. MS: calc'd 459 (M+H)⁺, measured 459 (M+H)⁺.

Preparation of 3-[(8aS)-3-oxo-1,5,6,7,8,8a-hexahydroimidazo[1,5-a]pyrazin-2-yl]-2,2-dimethyl-propanoic acid (compound 2B)

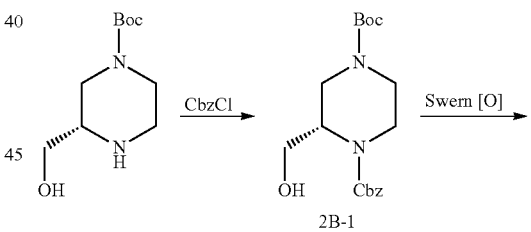

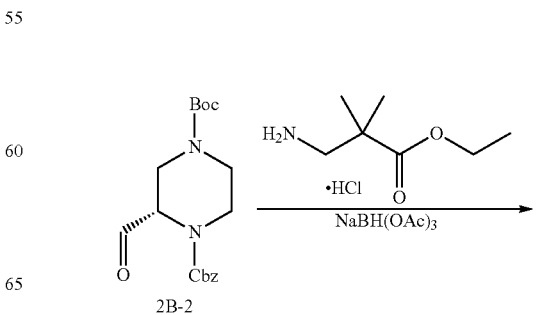

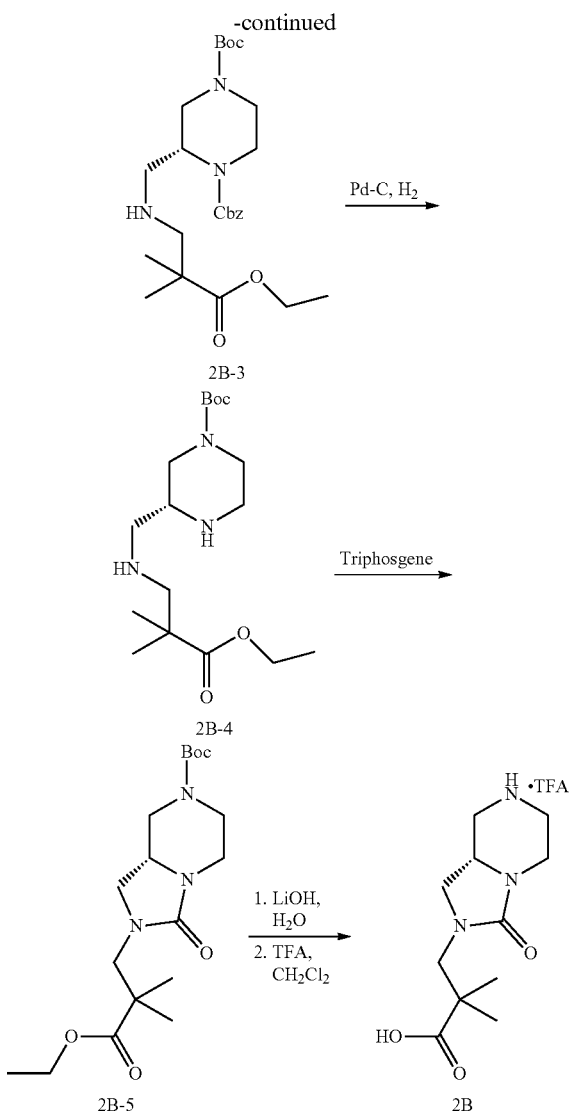

Preparation of O1-benzyl O4-tert-butyl (2S)-2-(hydroxymethyl)piperazine-1,4-dicarboxylate (compound 2B-1)

To a stirred solution of tert-butyl (3S)-3-(hydroxymethyl)piperazine-1-carboxylate (CAS number: 314741-40-7, Bepharm; for its synthesis, please refer to: Gao H., Renslo A. R. *J. Org. Chem.* 2007, 72, 8591-8592) (6 g, 27.8 mmol) in saturated NaHCO₃ (45 mL) and EtOAc (45 mL) was added benzyl chloroformate (7.1 g, 41.7 mmol) dropwise at 0° C. Then the reaction mixture was stirred at room temperature for 15 hours. The reaction mixture was diluted with EtOAc (60 mL). The organic layer was separated and the aqueous layer was extracted with EtOAc (35 mL). The combined organic layers were dried over Na₂SO₄. The solvent was removed in vacuo to give the crude product, which was purified by silica gel column chromatography (Petroleum ether:EtOAc=10:1 to 1:1) to give O1-benzyl O4-tert-butyl (2S)-2-(hydroxymethyl)piperazine-1,4-dicarboxylate (compound 2B-1, 6.7 g). MS: calc'd 351 (M+H)⁺, measured 351 (M+H)⁺.

Preparation of O1-benzyl O4-tert-butyl (2S)-2-formylpiperazine-1,4-dicarboxylate (compound 2B-2)

To a stirred solution of oxalyl chloride (3.64 g, 28.6 mmol) in anhydrous dichloromethane (80 mL) at −78° C. was added dropwise dimethyl sulfoxide (4.47 g, 57.3 mmol). After 10 minutes, a solution of O1-benzyl O4-tert-butyl (2S)-2-(hydroxymethyl)piperazine-1,4-dicarboxylate (compound 2B-1, 6.7 g, 19.1 mmol) in dichloromethane (20 mL) was added dropwise. After the mixture was stirred for 30 minutes at −78° C., N,N-diisopropylethylamine (14.78 g, 114.6 mmol) was added and the reaction mixture was stirred for 30 minutes. After the reaction mixture was slowly warmed to 0° C. over 30 minutes, it was diluted with dichloromethane (80 mL), washed with 5% aqueous citric acid (10 mL), brine and then dried over Na₂SO₄. After filtration, the mixture was concentrated in vacuo to get the crude product O1-benzyl O4-tert-butyl (2S)-2-formylpiperazine-1,4-dicarboxylate (compound 2B-2, 7.0 g). MS: calc'd 349 (M+H)⁺, measured 349 (M+H)⁺.

Preparation of O1-benzyl O4-tert-butyl (2R)-2-[[(3-ethoxy-2,2-dimethyl-3-oxo-propyl)amino]methyl]piperazine-1,4-dicarboxylate (compound 2B-3)

To a stirred solution of ethyl 3-amino-2,2-dimethyl-propanoate hydrochloride salt (3.4 g, 18.6 mmol) in anhydrous DCM (100 mL) was added DIPEA (2.6 g, 27.3 mmol) at room temperature. Then O1-benzyl O4-tert-butyl (2S)-2-formylpiperazine-1,4-dicarboxylate (compound 2B-2, crude, 7.0 g, 20 mmol) was added, followed by NaBH(OAc)₃ (6.3 g, 29.8 mmol) and AcOH (1.5 mL) at 0° C. The reaction mixture was stirred for 16 hours at room temperature. Water (100 mL) was added and the mixture was extracted with DCM (100 mL). The organic layer was dried and concentrated in vacuo to give crude product of O1-benzyl O4-tert-butyl (2R)-2-[[(3-ethoxy-2,2-dimethyl-3-oxo-propyl)amino]methyl]piperazine-1,4-dicarboxylate (compound 2B-3, 7.3 g). MS: calc'd 478 (M+H)⁺, measured 478 (M+H)⁺.

Preparation of tert-butyl (3R)-3-[[(3-ethoxy-2,2-dimethyl-3-oxo-propyl)amino]methyl]piperazine-1-carboxylate (compound 2B-4)

To a solution of O1-benzyl O4-tert-butyl (2R)-2-[[(3-ethoxy-2,2-dimethyl-3-oxo-propyl)amino]methyl]piperazine-1,4-dicarboxylate (compound 2B-3, crude, 3.3 g, 6.9 mmol) in EtOH (100 mL) was added 10% palladium on carbon (1 g). Then the mixture was stirred at 50° C. for 3 hours under hydrogen atmosphere (50 Psi). The reaction mixture was filtered and the filtrate was concentrated in vacuo to get the tert-butyl (3R)-3-[[(3-ethoxy-2,2-dimethyl-3-oxo-propyl)amino]methyl]piperazine-1-carboxylate (compound 2B-4, 1.8 g). MS: calc'd 344 (M+H)⁺, measured 344 (M+H)⁺.

Preparation of tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate (compound 2B-5)

To a solution of tert-butyl (3R)-3-[[(3-ethoxy-2,2-dimethyl-3-oxo-propyl)amino]methyl]piperazine-1-carboxylate (compound 2B-4, 1.8 g, 5.2 mmol) in anhydrous dichloromethane (60 mL) was added N,N-diisopropylethylamine (3.4 g, 26.2 mmol) at 0° C. Then triphosgene (783 mg, 2.6 mmol) was added at 0° C. and the mixture was stirred at 10-15° C. for 16 hours. Water (50 mL) was added and the mixture was extracted with dichloromethane (60 mL). The organic layer was dried over Na₂SO₄ and the solvent was removed in vacuo to give the crude product. The crude product was purified by silica gel column chromatography (Petroleum ether:EtOAc=5:1 to 1:1) to give tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate (compound 2B-5, 1.3 g). MS: calc'd 370 (M+H)⁺, measured 370 (M+H)⁺.

Preparation of 3-[(8aS)-3-oxo-1,5,6,7,8,8a-hexahydroimidazo[1,5-a]pyrazin-2-yl]-2,2-dimethyl-propanoic acid (compound 2B)

To a stirred solution of tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate (compound 2B-5, 94 mg, 0.25 mmol) in THF (3 mL) was added a solution of LiOH·H₂O (84 mg, 2.0 mmol) in H₂O (1 mL) at room temperature. After the reaction mixture was stirred at room temperature overnight, it was acidified to PH 3~4 with 1N HCl at 0° C. The mixture was then concentrated in vacuo and azeotropically dried with toluene to give the crude acid which was dissolved in dichloromethane (2 mL) and treated with trifluoroacetic acid (2 mL) at room temperature. After the reaction mixture was stirred at room temperature for 1 hour, the solvent was removed in vacuo to give 3-[(8aS)-3-oxo-1,5,6,7,8,8a-hexahydroimidazo[1,5-a]pyrazin-2-yl]-2,2-dimethyl-propanoic acid (compound 2B) which was used directly. MS: calc'd 242 (M+H)⁺, measured 242 (M+H)⁺.

Example 3

[(S)-[(2S,5R)-5-(5-amino-2-oxo-thiazolo[4,5-d]pyrimidin-3-yl)-1,3-oxathiolan-2-yl]-cyclopropyl-methyl] acetate (Compound 3)

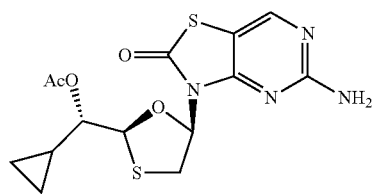

Compound 3 was prepared through following scheme:

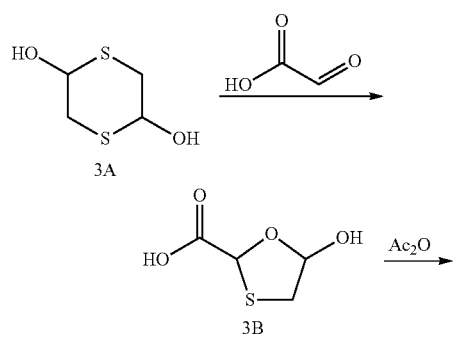

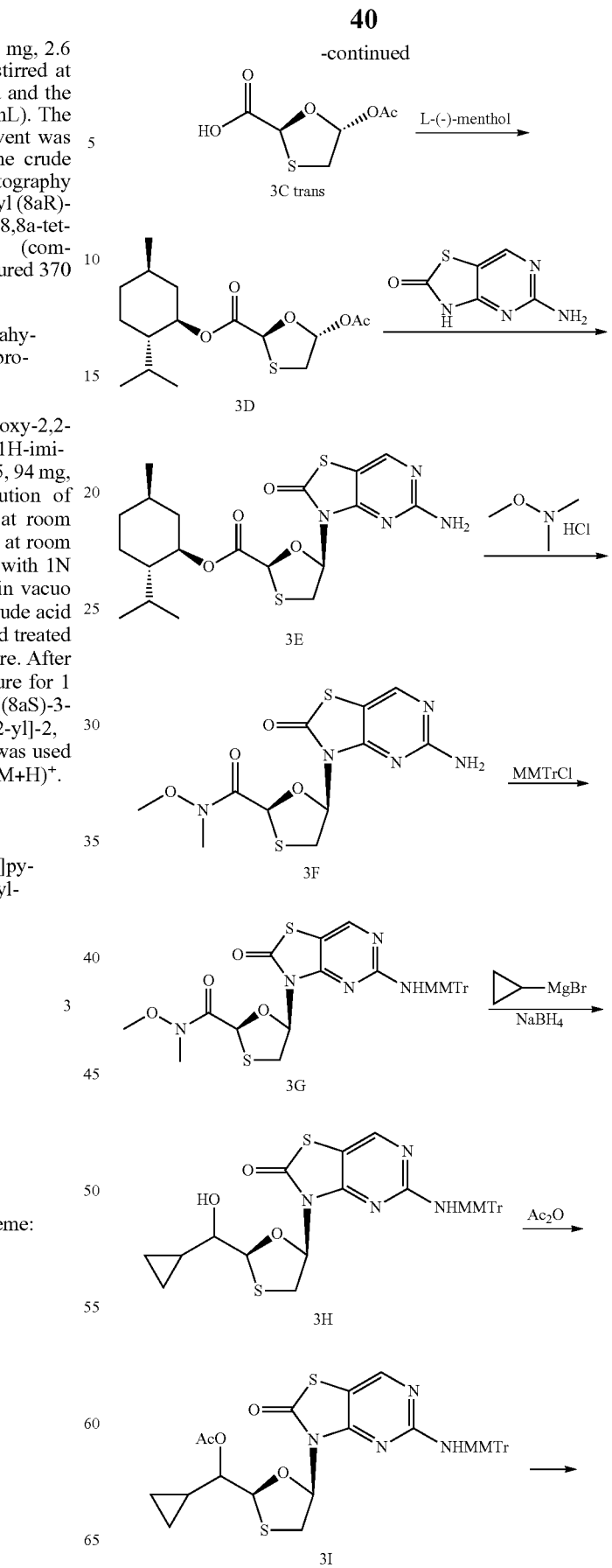

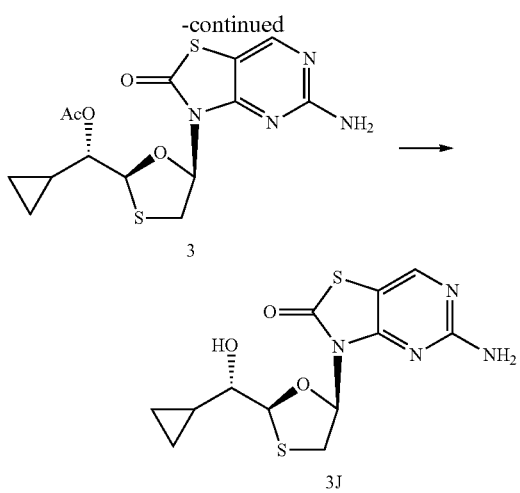

Preparation of
5-hydroxy-1,3-oxathiolane-2-carboxylic acid

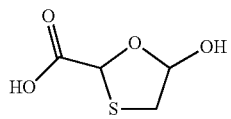

To a stirred solution of 1,4-dithiane-2,5-diol (compound 3A, 150 g, 0.98 mol) in methyl tert-butyl ether (500 mL) and cyclohexane (150 mL) was added glyoxylic acid (180 g, 1.96 mol). The resulting reaction mixture was stirred at 80° C. under Dean-Stark conditions for 16 hours. The resulting solution was concentrated in vacuo. The residue was purified by column chromatography on silica gel (eluting with 1:7 ethyl acetate in petroleum ether to 100% ethyl acetate) to afford 220 g of the crude 5-hydroxy-1,3-oxathiolane-2-carboxylic acid (compound 3B), which was used directly in the next step without further purification.

Preparation of
trans-5-acetoxy-1,3-oxathiolane-2-carboxylic acid

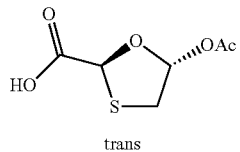

To a solution of 5-hydroxy-1,3-oxathiolane-2-carboxylic acid (compound 3B, 220 g, 1.5 mol) in HOAc (1.5 L) was added concentrated sulfuric acid (1 mL) and acetic anhydride (50 g, 0.5 mol). After being stirred at room temperature for 16 hours, the resulting reaction mixture was diluted with water and extracted with EtOAc. The organic phase was combined and concentrated in vacuo. The residue was purified by column chromatography on silica gel (eluting with 1:10 to 1:7 ethyl acetate in petroleum ether) to afford crude product, which was recrystallized from toluene to give 10 g of trans-5-acetoxy-1,3-oxathiolane-2-carboxylic acid (compound 3C trans). (For the synthesis, please also refer to: *J. Org. Chem.* 1995, 60, 2621-2623.)

Compound 3C Trans:

$^1$H NMR (400 MHz, DMSO-$d_6$) δppm: 13.26 (br, 1H), 6.66 (d, J=4.0 Hz, 1H), 5.66 (s, 1H), 3.30-3.37 (m, 1H), 3.19-3.25 (m, 1H), 2.04 (s, 3H).

Preparation of [(1R,2S,5R)-2-isopropyl-5-methyl-cyclohexyl] (2S,5S)-5-acetoxy-1,3-oxathiolane-2-carboxylate

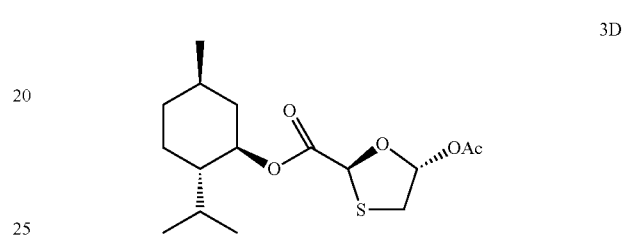

A solution of dicyclohexylcarbodiimide (12 g, 57 mmol) in DCM (50 mL) was added to a round bottom flask containing a solution of trans-5-acetoxy-1,3-oxathiolane-2-carboxylic acid (compound 3C trans, 10 g, 52 mmol), L-(−)-menthol (8.9 g, 57 mmol) and DMAP (0.6 g, 5.2 mmol) in DCM (100 mL) at 0° C. After the reaction mixture was stirred at room temperature for 16 hours, methanol (2 mL) and glacial acetic acid (2 mL) were added. The reaction mixture was stirred for another 10 minutes and then diluted with hexane (250 mL), filtrated through celite and the filtrate was concentrated to yield crude product. (*J. Org. Chem.* 1995, 60, 2621-2623). The crude product was re-dissolved in hexane (250 mL), filtered and the filtrate was concentrated in vacuo. The residue was purified by supercritical fluid chromatography (SFC) to give 3.2 g of [(1R,2S,5R)-2-isopropyl-5-methyl-cyclohexyl] (2S,5S)-5-acetoxy-1,3-oxathiolane-2-carboxylate (compound 3D) with a diastereoisomeric excess of 85% as a colorless oil. The diastereoisomeric excess value of compound 3D was obtained by HPLC (Agilent 1260 HPLC) analysis using a chiral column (CHIRALPAK IA-3 ODH (4.6 mm×250 mm, 5 μm)). The mobile phase of the chiral analysis was 20:80 acetonitrile in MeOH.

Compound 3D:

$^1$H NMR (400 MHz, CDCl$_3$) δppm: 6.81 (d, J=4.0 Hz, 1H), 5.63 (s, 1H), 4.76 (dt, J=10.9, 4.5 Hz, 1H), 3.44 (dd, J=11.7, 4.1 Hz, 1H), 3.17 (d, J=11.8 Hz, 1H), 2.11 (s, 3H), 2.00 (d, J=12.0 Hz, 1H), 1.85 (dt, J=6.9, 2.5 Hz, 1H), 1.69 (d, J=11.0 Hz, 2H), 1.55-1.26 (m, 3H), 1.11-1.00 (m, 2H), 0.91 (dd, J=6.8, 9.8 Hz, 6H), 0.76 (d, J=7.0 Hz, 3H).

Preparation of [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate

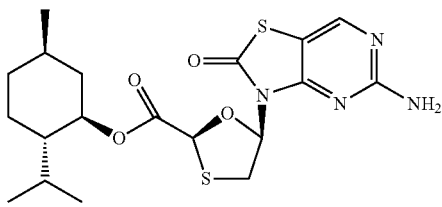

3E

A suspension of 5-amino-3H-thiazolo[4,5-d]pyrimidin-2-one (6.0 g, 36 mmol) and BSA (24.0 g, 118 mmol) in DCE (250 mL) was heated at 85° C. for 1 hour. The reaction mixture was cooled to 0° C., to the above mixture was added a solution of [(1R,2S,5R)-2-isopropyl-5-methyl-cyclohexyl] (2S,5S)-5-acetoxy-1,3-oxathiolane-2-carboxylate (compound 3D, 9.0 g, 27 mmol) in DCE (10 mL), followed by TMSI (14 g, 70 mmol) dropwise. The reaction mixture was stirred at 60° C. for 5 hours, quenched by aqueous NaHCO$_3$ solution, and then extracted with EtOAc. The organic layer was washed with brine, dried over anhydrous Na$_2$SO$_4$ and concentrated to give the crude product as an oil, which was purified by column chromatography on silica gel (eluting with 1:100 to 1:50 methanol in dichloromethane) to give 7.7 g of a mixture of two isomers, which was further purified and separated by preparative HPLC to give the desired 2.8 g of beta isomer [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate (compound 3E) as a white solid. The configuration of compound 3E was determined by NOESY.

Compound 3E:
$^1$H NMR (400 MHz, CDCl$_3$) δppm: 8.17 (s, 1H), 6.44 (m, 1H), 5.51 (s, 1H), 5.12 (bs, 2H), 4.78 (m, 1H), 4.47 (m, 1H), 3.16 (m, 1H), 2.00 (m, 1H), 1.79 (m, 1H), 1.62 (m, 2H), 1.38 (m, 2H), 0.98 (m, 2H), 0.9-0.72 (m, 10H). MS obsd. (ESI$^+$) [(M+H)$^{+1:}$ 439.

Preparation of (2S,5R)-5-(5-amino-2-oxo-thiazolo[4,5-d]pyrimidin-3-yl)-N-methoxy-N-methyl-1,3-oxathiolane-2-carboxamide

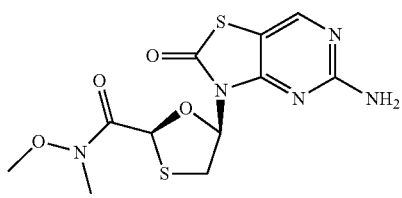

3F

A solution of [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate (compound 3E, 3.0 g, 7.5 mmol) in 80% TFA aqueous (20 mL) was stirred at 50° C. for 16 hours, and then concentrated to give the crude acid as a white solid, which was re-dissolved in THF (40 mL). To the above mixture was added N-methoxymethylamine hydrochloride (2.1 g, 22 mmol), DIPEA (14.5 g, 112 mmol) and HATU (8.36 g, 22 mol) at room temperature. After being stirred at room temperature for 16 hours, the reaction mixture was diluted with DCM, washed by water and brine, dried over anhydrous Na$_2$SO$_4$, and concentrated to give the crude product which was purified by flash chromatography on silica gel (eluting with 1:100 to 1:50 methanol in dichloromethane) to give 2.1 g of (2S,5R)-5-(5-amino-2-oxo-thiazolo[4,5-d]pyrimidin-3-yl)-N-methoxy-N-methyl-1,3-oxathiolane-2-carboxamide (compound 3F) as a white solid.

Compound 3F:
$^1$H NMR (400 MHz, CDCl$_3$) δppm: 8.16 (s, 1H), 6.42 (m, 1H), 5.83 (s, 1H), 5.14 (bs, 2H), 4.46 (t, J=9.6 Hz, 1H), 3.72 (s, 3H), 3.23 (s, 3H), 3.15 (m, 1H). MS obsd. (ESI$^+$) [(M+H)$^{+1:}$ 344.

Preparation of (2S,5R)—N-methoxy-5-[5-[[(4-methoxyphenyl)-diphenyl-methyl]amino]-2-oxo-thiazolo[4,5-d]pyrimidin-3-yl]-N-methyl-1,3-oxa-thiolane-2-carboxamide

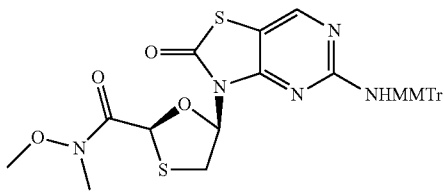

3G

To a solution of (2S,5R)-5-(5-amino-2-oxo-thiazolo[4,5-d]pyrimidin-3-yl)-N-methoxy-N-methyl-1,3-oxathiolane-2-carboxamide (compound 3F, 2.1 g, 6.1 mmol) in DCM (30 mL) was added collidine (1.45 g, 12 mmol), AgNO$_3$ (2.04 g, 12 mmol) and MMTrCl (3.8 g, 12 mmol) at room temperature. After being stirred at room temperature for 16 hours, the reaction mixture was diluted with DCM, filtered to remove the solid. The filtrate was washed with water and brine, dried over anhydrous Na$_2$SO$_4$ and concentrated to give the crude product, which was purified by flash chromatography on silica gel (eluting with 1:100 to 2:1 ethyl acetate in petroleum ether) to give 3.6 g of (2S,5R)—N-methoxy-5-[5-[[(4-methoxyphenyl)-diphenyl-methyl]amino]-2-oxo-thiazolo[4,5-d]pyrimidin-3-yl]-N-methyl-1,3-oxathiolane-2-carboxamide (compound 3G) as a yellow solid. (ESI$^+$) [(M+H)$^{+1:}$ 616.

Preparation of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one

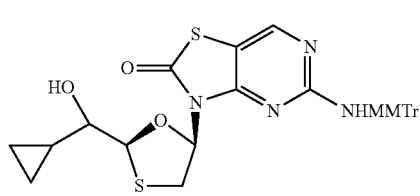

3H

To a solution of (2S,5R)—N-methoxy-5-[5-[[(4-methoxyphenyl)-diphenyl-methyl]amino]-2-oxo-thiazolo[4, 5-d]pyrimidin-3-yl]-N-methyl-1,3-oxathiolane-2-carboxamide (compound 3G, 3 g, 5 mmol) in THF (40 mL) was added Grignard reagent, cyclopropylmagnesium bromide (0.5 M, 25 mL) at 0° C. The reaction mixture was stirred at 0° C. for 30 min. The reaction was quenched with saturated NH₄Cl solution and extracted with EtOAc. The organic layer was dried and concentrated to give the crude product, which was re-dissolved in MeOH (50 mL). To the above mixture was added NaBH₄ (2.0 g, 540 mmol) at 0° C. The reaction mixture was stirred at room temperature for 30 min. The reaction was quenched with saturated NH₄Cl solution and extracted with DCM. The organic layer was dried over anhydrous Na₂SO₄ and concentrated to give the crude product, which was purified by flash chromatography on silica gel (eluting with 1:100 to 1:1 ethyl acetate in petroleum ether) to give 1.8 g of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (compound 3H) as a yellow solid. (ESI⁺) [(M+H)⁺]: 599.

Preparation of [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl] acetate

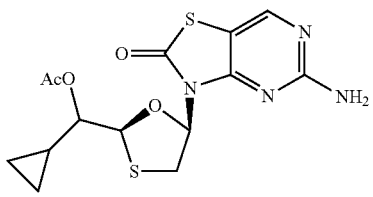

3I

To a solution of 3-[(2S,5R)-2-[cyclopropyl(hydroxy)methyl]-1,3-oxathiolan-5-yl]-5-[[(4-methoxy phenyl)-diphenyl-methyl]amino]thiazolo[4,5-d]pyrimidin-2-one (compound 3H, 1.2 g, 2 mmol) in DCM (10 mL) was added TEA (800 mg, 8 mmol), DMAP (30 mg, 0.2 mmol) and Ac₂O (400 mg, 4 mmol) at 0° C. The reaction mixture was stirred at room temperature for 48 hours. After the reaction was completed, the reaction was quenched by water, extracted with DCM. The organic layer was dried and concentrated to give 1.3 g of the crude product [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl] acetate (compound 3I) as a white solid, which was used directly in the next step without further purification. (ESI⁺) [(M+H)⁺]: 641.

Preparation of [(S)-[(2S,5R)-5-(5-amino-2-oxo-thiazolo[4,5-d]pyrimidin-3-yl)-1,3-oxathiolan-2-yl]-cyclopropyl-methyl] acetate

3

A solution of [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl] acetate (compound 3I, 1.3 g, 2 mmol) in 90% HCOOH aqueous solution (25 mL) was stirred at room temperature for 1 hour. The reaction mixture was concentrated and the residue was further purified and separated by preparative HPLC to give 114 mg of [(S)-[(2S,5R)-5-(5-amino-2-oxo-thiazolo[4,5-d]pyrimidin-3-yl)-1,3-oxathiolan-2-yl]-cyclopropyl-methyl] acetate (compound 3) as a white solid.

Compound 3:
¹H NMR (400 MHz, Methanol-d₄) δppm: 8.20 (s, 1H), 6.34 (m, 1H), 5.34 (d, J=6.4 Hz, 1H), 4.54 (t, J=6.0 Hz, 1H), 4.18 (t, J=8.4 Hz, 1H), 3.31 (t, J=6.0 Hz, 1H), 2.02 (s, 3H), 1.13 (m, 1H), 0.65-0.42 (m, 4H). MS obsd. (ESI⁺) [(M+Na)⁺]: 391.

Preparation of 5-amino-3-[(2S,5R)-2-[(S)-cyclopropyl(hydroxy)methyl]-1,3-oxathiolan-5-yl]thiazolo[4,5-d]pyrimidin-2-one

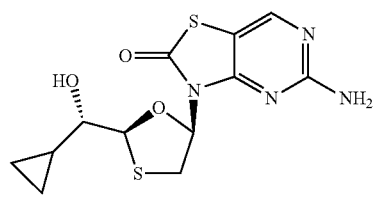

3J

To a solution of [(S)-[(2S,5R)-5-(5-amino-2-oxo-thiazolo[4,5-d]pyrimidin-3-yl)-1,3-oxathiolan-2-yl]-cyclopropyl-methyl] acetate (compound 3, 500 mg, 1.36 mmol) in methanol (5 mL) was added K₂CO₃ (94 mg, 0.68 mmol). After being stirred at room temperature for 4 hours, the reaction was quenched with HOAc to pH 7 and then concentrated in vacuo. The residue was diluted with EtOAc and filtered. The filtrate was concentrated in vacuo. The residue was purified and separated by preparative HPLC to give 45 mg of 5-amino-3-[(2S,5R)-2-[(S)-cyclopropyl(hydroxy)methyl]-1,3-oxathiolan-5-yl]thiazolo[4,5-d]pyrimidin-2-one (compound 3J) as a white powder.

Figure 3:
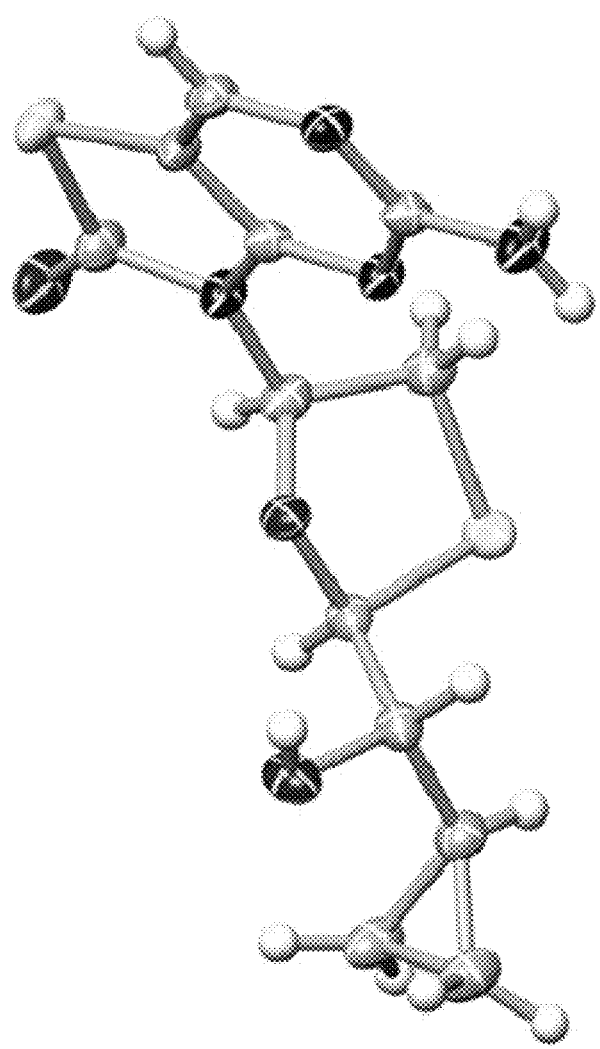
FIG. 3: X-ray crystal structure of Compound 3J.

Compound 3J:
The absolute structure was determined by ¹H NMR and single crystal X-ray structural analysis as shown in FIG. 3. ¹H NMR (400 MHz, Methanol-d₄) δppm: 8.25 (s, 1H), 6.39 (dd, J=9.16, 5.65 Hz, 1H), 5.24 (d, J=5.27 Hz, 1H), 4.06 (dd, J=10.29, 9.29 Hz, 1H), 3.13-3.30 (m, 2H), 0.37-1.04 (m, 5H). MS obsd. (ESI⁺) [(M+H)⁺]: 327.0.

Example 4

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Compound 4)

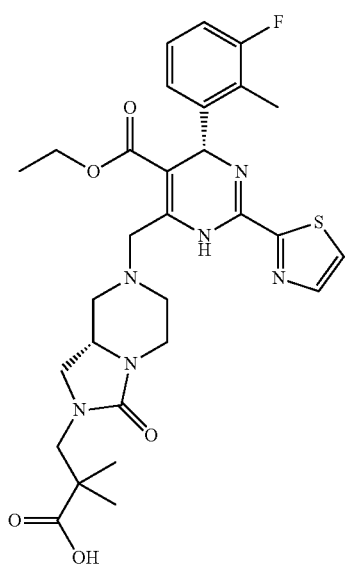 [SMILES: CCOC(=O)C1=C(CN2CCN3C(=O)N(CC(C)(C)C(=O)O)C[C@@H]3C2)NC(c2nccs2)=N[C@H]1c1cccc(F)c1C]

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Compound 4)

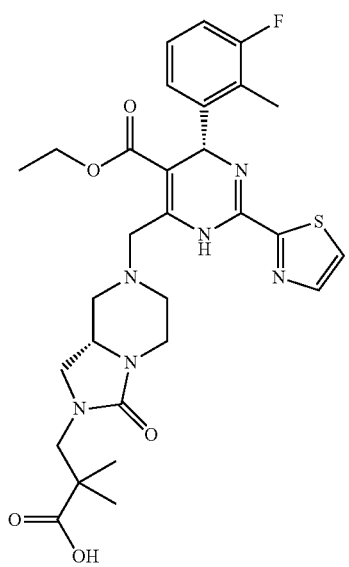 [SMILES: CCOC(=O)C1=C(CN2CCN3C(=O)N(CC(C)(C)C(=O)O)C[C@@H]3C2)NC(c2nccs2)=N[C@H]1c1cccc(F)c1C]

Compound 4 was prepared through following scheme:

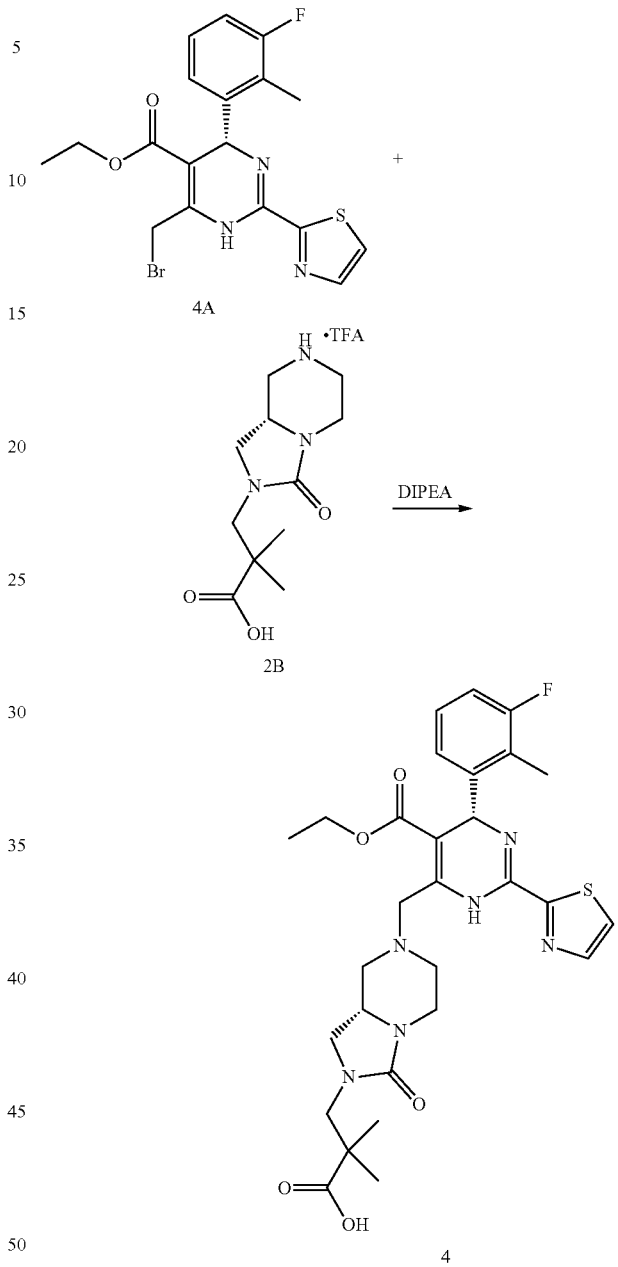

The title compound was prepared in analogy to Compound 2 by using ethyl (4S)-6-(bromomethyl)-4-(3-fluoro-2-methyl-phenyl)-2-thiazol-2-yl-1,4-dihydropyrimidine-5-carboxylate (compound 4A) instead of ethyl (4R)-6-(bromomethyl)-4-(2-chloro-3-fluoro-phenyl)-2-thiazol-2-yl-1,4-dihydropyrimidine-5-carboxylate (compound 2A). Compound 4 was obtained as a light yellow solid (132 mg). $^1$H NMR (400 MHz, Methanol-$d_4$) δppm 7.95 (d, J=3.3 Hz, 1H), 7.75 (d, J=3.3 Hz, 1H), 7.08-7.23 (m, 2H), 6.95 (t, J=8.8 Hz, 1H), 5.99 (s, 1H), 4.02-4.17 (m, 3H), 3.79-4.00 (m, 3H), 3.36-3.57 (m, 2H), 3.26-3.33 (m, 1H), 3.17-3.25 (m, 1H), 3.11 (dd, J=9.3, 4.0 Hz, 1H), 2.78-2.99 (m, 2H), 2.53 (d, J=2.0 Hz, 3H), 2.39 (dd, J=11.2, 8.2 Hz, 1H), 2.14-2.26 (m, 1H), 1.21 (d, J=2.8 Hz, 6H), 1.15 ppm (t, J=7.2 Hz, 3H). MS: calc'd 599 (M+H)$^+$, measured 599 (M+H)$^+$.

Preparation of ethyl (4S)-6-(bromomethyl)-4-(3-fluoro-2-methyl-phenyl)-2-thiazol-2-yl-1,4-dihydropyrimidine-5-carboxylate (compound 4A)

Compound 4A was prepared in analogy to compound 2A by using 2-methyl-3-fluorobenzaldehyde instead of 2-chloro-3-fluorobenzaldehyde. The optical rotation of compound 4A: $[\alpha]_D^{20}$ −21.0 (c 0.10, MeOH).

Example 5

5-amino-3-[(2R,3R,5S)-3-hydroxy-5-[(1S)-1-hydroxypropyl]tetrahydrofuran-2-yl]-6H-thiazolo[4,5-d]pyrimidine-2,7-dione (compound 11)

Compound 11

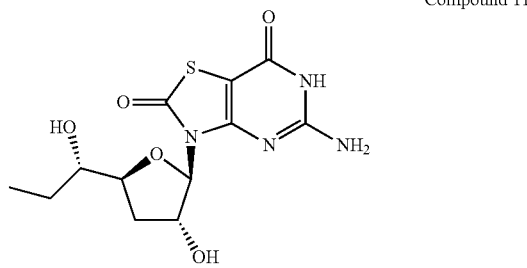

Compound 11 was prepared according to the following Scheme.

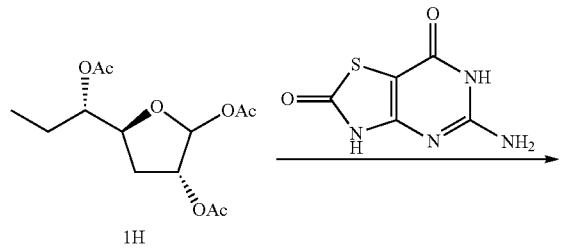

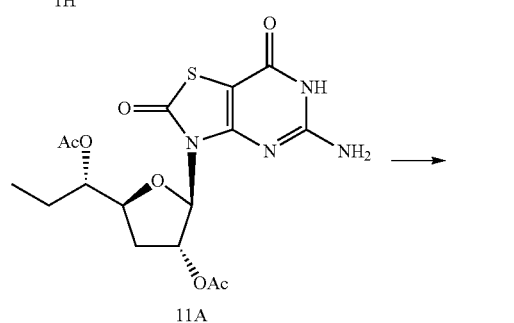

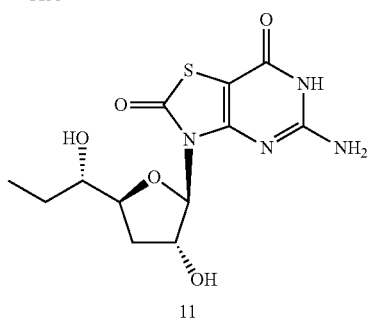

Preparation of [(2R,3S,5S)-5-[(1S)-1-acetoxypropyl]-2-(5-amino-2,7-dioxo-6H-thiazolo[4,5-d]pyrimidin-3-yl)tetrahydrofuran-3-yl] acetate

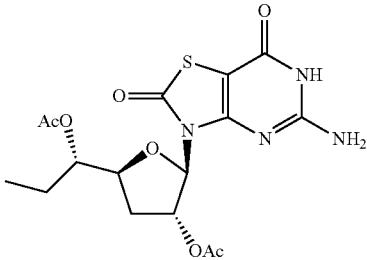 [SMILES: CC[C@H](O)[C@@H]1C[C@@H](O)[C@H](n2c(=O)sc3c(=O)[nH]c(N)nc32)O1]

11A

To a suspension of 5-amino-3,6-dihydrothiazolo[4,5-d]pyrimidine-2,7-dione (5.37 g, 29.1 mmol) and [(3R,5S)-2-acetoxy-5-[(1S)-1-acetoxypropyl]tetrahydrofuran-3-yl] acetate (compound 1H, 2.8 g, 9.7 mmol) in acetonitrile (140 mL) was added BSA (21.4 mL, 87.3 mmol). The reaction mixture was stirred at 65° C. for 1.5 hour under argon to form a clear solution. Then to the solution was added TMSOTf (9.8 g, 43.7 mmol) and the mixture was stirred at 65° C. for another 3 hours. The reaction was concentrated in vacuum. The residue was dissolved in EtOAc (200 mL) and extracted with saturated NaHCO$_3$ solution (50 mL). A precipitate was out of the organic layer. The resulting mixture was filtered and the filtrate was washed with brine (50 mL), dried over Na$_2$SO$_4$ and concentrated in vacuum to give 2.3 g of the crude product [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate (compound 11A) as a yellow solid. MS obsd. (ESI$^-$) [(M+H)$^+$]: 413.1.

Preparation of 5-amino-3-[(2R,3R,5S)-3-hydroxy-5-[(1S)-1-hydroxypropyl]tetrahydrofuran-2-yl]-6H-thiazolo[4,5-d]pyrimidine-2,7-dione

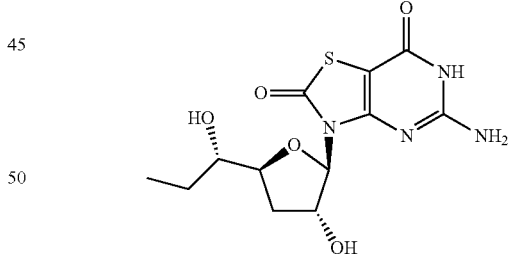

To a solution of [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate (compound 11A, 2.3 g, 5.58 mmol) in methanol (100 mL) was added sodium methoxide (1.5 g, 27.9 mmol) After the addition, the mixture was stirred at room temperature for 1.5 hours (monitored by TLC). After the reaction was completed, the reaction was quenched with saturated aqueous NH$_4$Cl (50 mL). The resulting mixture was concentrated in vacuum to remove most of MeOH. The residue was extracted with EtOAc (100 mL) ten times. The combined organic layer was washed with brine (100 ml), dried over Na$_2$SO$_4$ and concentrated in vacuum. The residue was purified by silica gel column eluted with DCM/

MeOH=20/1 to 10/1 to give 360 mg of 5-amino-3-[(2R,3R,5S)-3-hydroxy-5-[(1S)-1-hydroxypropyl]tetrahydrofuran-2-yl]-6H-thiazolo[4,5-d]pyrimidine-2,7-dione (Compound 11) as a white solid and 550 mg of crude product.

Compound 11:
$^1$H NMR (400 MHz, DMSO-d$_6$) δ 11.22 (br s, 1H), 6.95 (br s, 2H), 5.72 (d, J=2.26 Hz, 1H), 5.42 (d, J=4.52 Hz, 1H), 4.73 (m, 1H), 4.53 (d, J=6.02 Hz, 1H), 3.96 (m, 1H), 3.25-3.32 (m, 1H), 2.25-2.48 (m, 1H), 1.66-1.74 (m, 1H), 1.35-1.46 (m, 1H), 1.19-1.31 (m, 1H), 0.88 (t, J=7.28 Hz, 3H)

Example 6

HEK293-Blue-hTLR-7 Cells Assay:

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β□ minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7 for 20 hours. The cell culture supernatant SEAP reporter activity was determined using QUANTI-Blue™ kit (Cat.#: rep-qb1, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 h. Then the HEK293-Blue-hTLR-7 cells were incubated with addition of 20 μL test compound in a serial dilution in the presence of final DMSO at 1% and perform incubation under 37° C. in a CO$_2$ incubator for 20 hours. Then 20 μL of the supernatant from each well was incubated with 180 μL Quanti-blue substrate solution at 37° C. for 2 hours and the absorbance was read at 620655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

The TLR7 agonism activity in HEK293-hTLR-7 assay of compound 11 was 72 μM.

Example 6

A Combination of TLR7 Agonist (Compound 1) and HBV Capsid Assembly Inhibitor (Compound 2) Potently Reduced HBV DNA and HBsAg in AAV-HBV Mouse Model Animal Model 4-week old male C57BL/6 mice, specific pathogen free, were purchased from Shanghai Laboratory Animal Center of Chinese Academy of Sciences (SLAC) and housed in an animal care facility in individually ventilated cages under controlled temperature and light conditions following the Institutional Animal Care guidelines. AAV/HBV virus was purchased from Beijing FivePlus Molecular Medicine Institute (Beijing, China). This recombinant virus carries 1.3 copies of the HBV genome, which was packaged in AAV serotype 8 (AAV8) capsids. C57BL/6 mice were injected with 2004, of recombinant virus, diluted in saline buffer, through tail vein injection. The mice were bled at days 7 and 14 post injection to monitor HBV surface antigen (HBsAg), HBV e antigen (HBeAg), HBs antibody (HBsAb) and HBV genomic DNA in serum, and then were randomly grouped according to these HBV biomarkers.

Measurement of HBV Biomarkers

Serum HBsAg and HBeAg was measured using CLIA kits (Autobio Diagnostics Co., Ltd, Zhengzhou, China) according to the manufacturer's instructions. The lower limit of detection for HBsAg and HBeAg was 0.1 ng/mL and 0.25 NCU/mL (national clinical unit/mL) respectively. Serum dilution of 100-fold (for HBsAg) or 500-fold (for HBeAg) was used to obtain values within the linear range of the standard curve. Serum HBV DNA was extracted using a MagNA Pure 96 DNA and Viral NA Small Volume Kit (Roche) following the manufacturer's instructions. The DNA samples were analyzed by real-time quantitative PCR (qPCR) using a HBV-specific primer and probe set for specific amplification and detection of a 128 bp HBV genome region from the nucleotide 2969 to 3096. The sequences of the primers and probe are shown as follows:

```
Forward primer:
AAGAAAAACCCCGCCTGTAA;

Reverse primer:
CCTGTTCTGACTACTGCCTCTCC;

HBV-Probe:
5'TARMA-CCTGATGTGATGTTCTCCATGTTCAGC-BHQ2-3'.
```

Anti-HBs in the serum was measured on day 24 after the treatment ended using Anti-HBs CLIA kits (Autobio Diagnostics Co., Ltd, Zhengzhou, China) following the manufacturer's instructions. The serum samples were 3-fold diluted and 50 μL of the diluted samples were used for the assay.

Experiment Design and Results 10 mg/mL of Compound 1 and 1.2 mg/mL of Compound 2 was formulated as an inclusion complex with 2% Klucel LF, 0.1% Polysorbate 80, and 0.1% Parabens in water. All the mice were orally dosed for a total of 6 weeks followed by a 2-week off-treatment period. In one single-treatment control study, the five mice of the group Compound 1 were treated with Compound 1 at 100 mg/kg every other day (QOD). The vehicle group was treated with an equivalent volume of oral-QD vehicle placebo (2% Klucel LF, 0.1% Polysorbate 80, and 0.1% Parabens in water). In the combination therapy study, the five mice of the group Compound 2 were administered at 12 mg/kg orally once daily (QD). The group Combo received 100 mg/kg of Compound 1 QOD plus 12 mg/kg Compound 2 QD. The vehicle group was treated with an equivalent volume of oral-QD vehicle placebo (2% Klucel LF, 0.1% Polysorbate 80, and 0.1% Parabens in water).

A mouse model with high level expression of both HBV DNA and HBsAg was generated by injecting C57BL/6 mice with a recombinant adeno-associated virus (AAV) carrying a replicable HBV genome (AAV-HBV). At 3 weeks post infection, persistent HBV viral markers such as HBV genomic DNA, HBsAg, and HBeAg were detected in the sera of the infected mice. With the long-lasting HBV viremia and a fully competent immune system, the AAV-HBV model was used to investigate the individual and combined effect of Compound 1, a prodrug of a TLR7 agonist, the active form of which, after conversion, induces potent innate immune responses, and Compound 2, a small molecule which inhibits HBV capsid assembly. As shown in FIG. 1, after a 6-week treatment, Compound 1 induced more than 2-log reduction in HBV DNA and more than 1-log reduction in HBsAg. Compound 2 alone reduced HBV DNA by more than 3-log and to the level below the LLQ (lower limit of quantification), and moderately reduced the HBsAg level. The combination of the Compound 1 and Compound 2 resulted in a sustainable reduction in both HBV DNA and HBsAg to the level below the LLQ even at the end of a 2-week off-treatment period. The results provide evidence for the synergistic antiviral effect of the novel therapy with the combination treatment of a TLR7 agonist and a HBV capsid assembly inhibitor.

Example 7

A Combination of TLR7 Agonist (Compound 1 and 3) and HBV Capsid Assembly Inhibitor (Compound 4 and 5) Potently Reduced HBV DNA and HBsAg in AAV-HBV Mouse Model In another independent study, more combinations of a TLR7 agonist plus a Capsid inhibitor and corresponding single compound treatments were tested (summarized in Table 2) using the same AAV-HBV mouse model and method of measurement of HBV biomarkers described in Example 5.

TABLE 2

Combination study design in AAV-HBV mouse model for Compound 1, 3, 4 and 5

| Group # | Mice# | Treatment Compound | Dose (mg/kg) | Drug delivery |
|---|---|---|---|---|
| 1 | 8 | vehicle | 0 | PO, QOD, 42D |
| 2 | 8 | Compound 1 | 100 | |
| 3 | 8 | Compound 4 | 20 | PO, QD, 42D |
| 4 | 8 | Compound 3 | 30 | PO, QOD, 42D |
| 5 | 8 | Compound 5 | 12 | PO, QD, 42D |
| 6 | 8 | Compound 1 | 100 | PO, QOD, 42D |
|   |   | Compound 4 | 20 | PO, QD, 42D |
| 7 | 8 | Compound 3 | 30 | PO, QOD, 42D |
|   |   | Compound 4 | 20 | PO, QD, 42D |
| 8 | 8 | Compound 1 | 100 | PO, QOD, 42D |
|   |   | Compound 5 | 12 | PO, QD, 42D |

In this study, eight mice were recruited in each group, and animals received the first dose on day 28 post AAV-HBV infection. The tested combinations included Compound 1 plus Compound 4, Compound 3 plus Compound 4, and Compound 1 plus Compound 5. All compounds were formulated as an inclusion complex with 2% Klucel LF, 0.1% Polysorbate 80, and 0.1% Parabens in water, and an equivalent volume of placebo containing 2% Klucel LF, 0.1% Polysorbate 80, and 0.1% Parabens was used in the vehicle group. Specifically, for the combination of Compound 1 plus Compound 4, 10 mg/mL of Compound 1 and 2 mg/mL of Compound 4 was formulated. The group Compound 1 was orally dosed at 100 mg/kg QOD, while the group Compound 4 were orally dosed at 20 mg/kg QD. The corresponding Combo group received 100 mg/kg of Compound 1 QOD plus 20 mg/kg Compound 4 QD. For the combination of Compound 3 plus Compound 4, 3 mg/mL of Compound 3 and 2 mg/mL of Compound 4 was formulated. The group Compound 3 were orally dosed at 30 mg/kg QOD, while the group Compound 4 were orally dosed at 20 mg/kg QD. The corresponding Combo group received 30 mg/kg of Compound 3 QOD plus 20 mg/kg Compound 4 QD. For the combination of Compound 1 plus Compound 5, 10 mg/mL of Compound 1 and 1.2 mg/mL of Compound 5 was formulated. The group Compound 1 were orally dosed at 100 mg/kg QOD, while the group Compound 5 were orally dosed at 12 mg/kg QD. The corresponding Combo group received 100 mg/kg of Compound 1 QOD plus 12 mg/kg Compound 5 QD. After the first dose, mice were submandibularly bled (75 µL blood/mouse) twice per week for serum collection until the end of the studies. The collected blood were left at 37° C. for at least 30 minutes to coagulate and then centrifuged at 13,200×g, 4° C. for 3 minutes to obtain mouse serum. These serum samples were subjected to analysis of HBV biomarkers.

Figure 4:
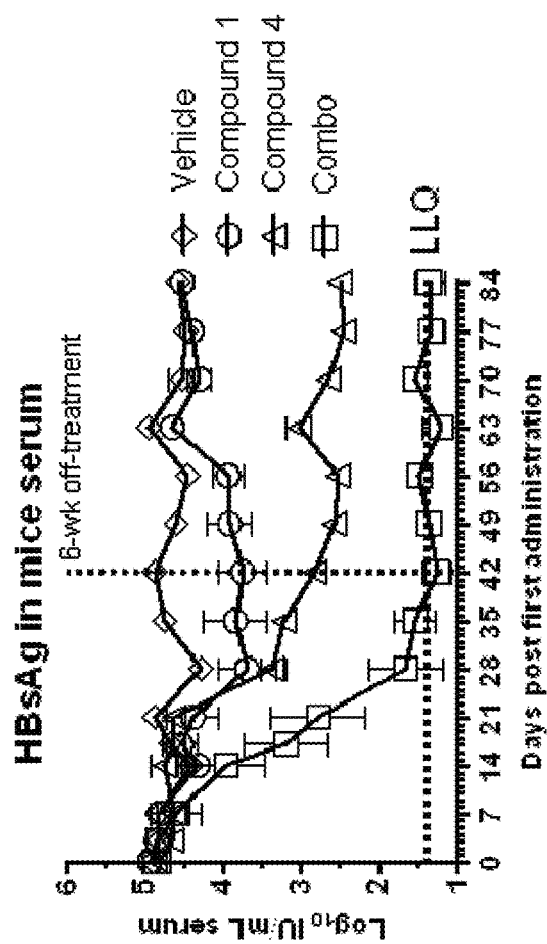
FIG. 4: HBV DNA and HBsAg in the AAV-HBV infected mice treated with vehicle, Compound 1 (100 mg/kg), Compound 4 (20 mg/kg), or the combination of Compound 1 plus Compound 4. The treatment started after the mice were infected with AAV-HBV for 4 weeks. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.
Figure 4:
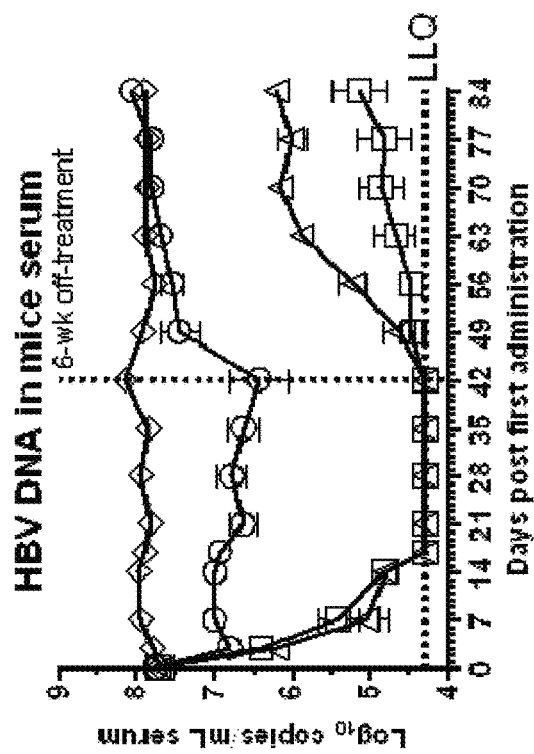
Figure 7:
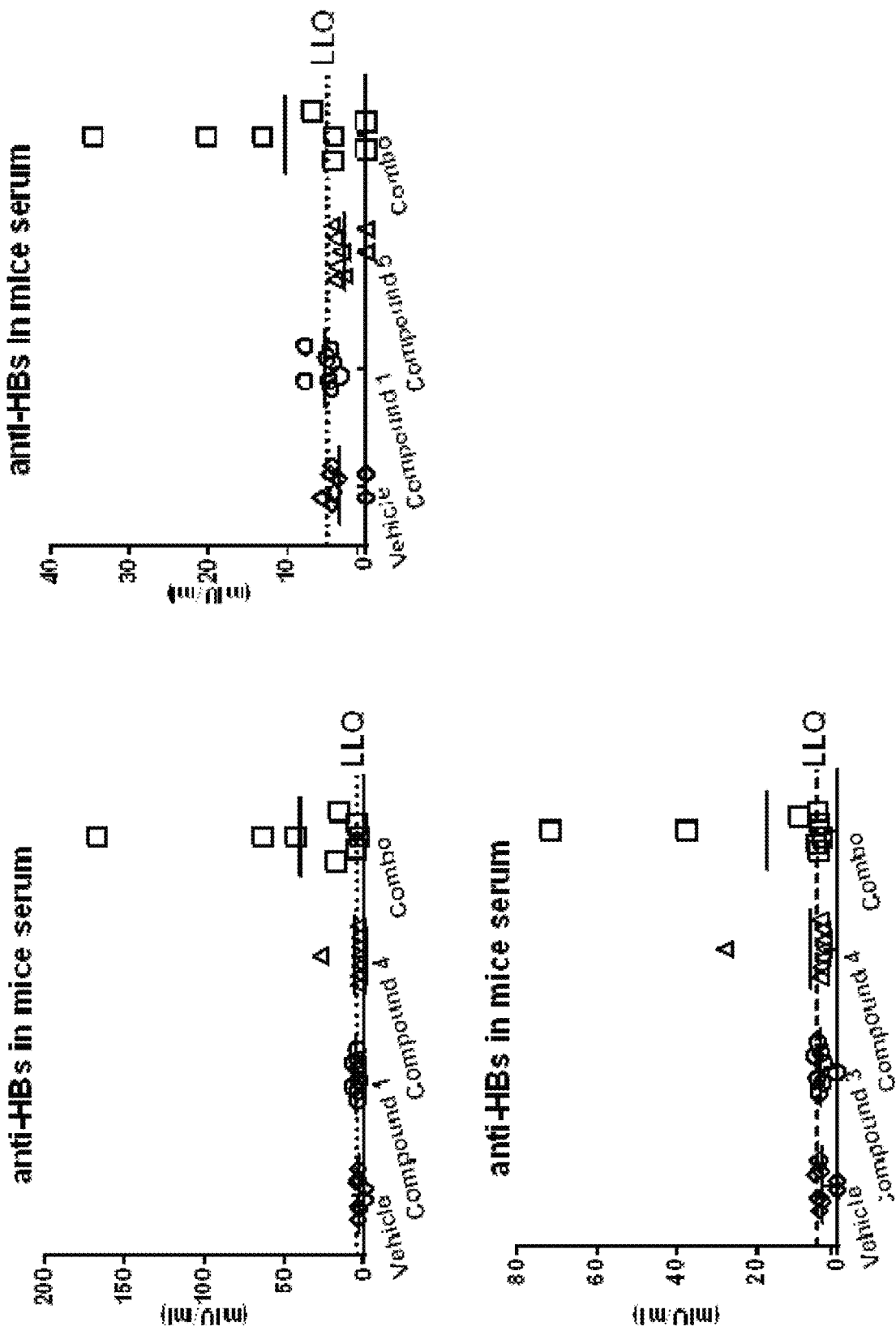
FIG. 7: The level of anti-HBs antibody (antibody against HBsAg) in the serum of each mouse taking the single or combination treatment as described in FIGS. 4, 5, and 6. The serum samples were collected on day 24 post the removal of treatment and anti-HBs was measured by anti-HBs CLIA. LLQ: lower limit of quantification.

As shown in FIG. 4, single treatment of Compound 4 at 20 mg/kg inhibited HBV DNA and reduced HBsAg by 2-log at the end of 6-week treatment. The combination of Compound 1 (TLR7 agonist) plus Compound 4 (HBV capsid inhibitor) clearly demonstrated a superior antiviral effect especially in controlling the HBsAg. In all animals taking the combination therapy, their HBsAg dropped to the level close to or below the LLQ within 4 weeks of the treatment, and a more than 3.5-log HBsAg reduction at the end of the treatment could last for at least 6 weeks during the off-treatment period. During the off-treatment period, 6 out of 8 mice were found to have developed detectable levels of anti-HBs, as shown in FIG. 7.

Figure 5:
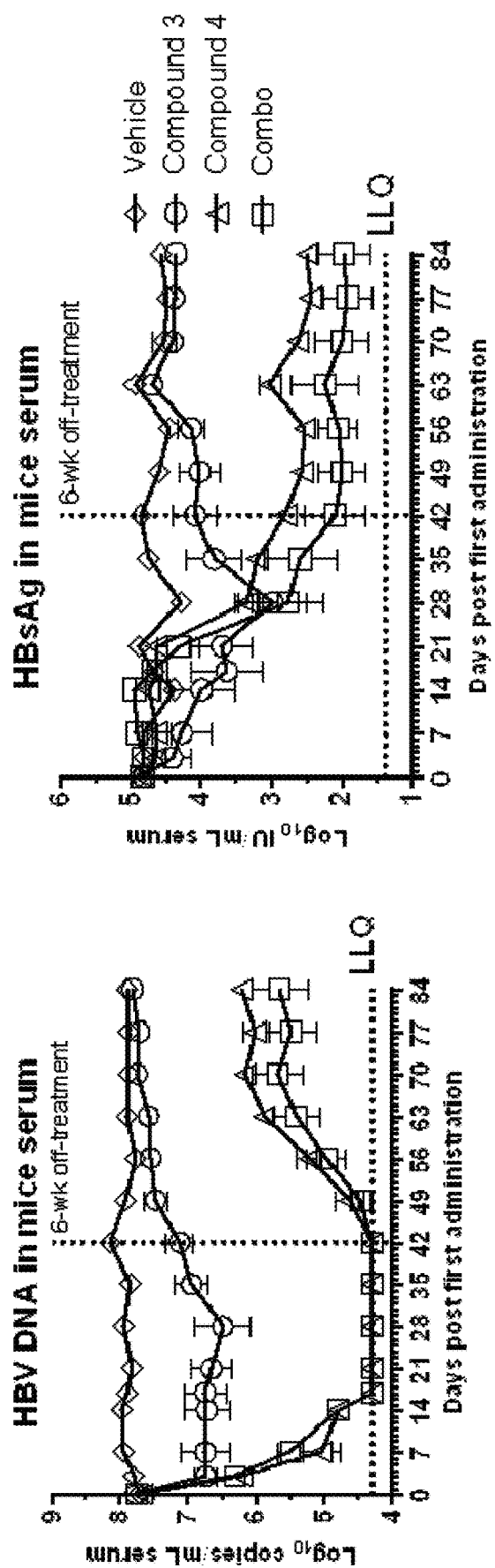
FIG. 5: HBV DNA and HBsAg in the AAV-HBV infected mice treated with vehicle, Compound 3 (30 mg/kg), Compound 4 (20 mg/kg), or the combination of Compound 3 plus Compound 4. The treatment started after the mice were infected with AAV-HBV for 4 weeks. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.

As shown in FIG. 5, another TLR7 agonist Compound 3 also reduced both HBV DNA and HBsAg. The combination of Compound 3 plus the capsid inhibitor Compound 4 exhibited further reduction in HBV DNA (>4 log) and in HBsAg (2.7-log). As shown in FIG. 7, 3 out of 8 mice taking Compound 3 plus Compound 4 developed detectable levels of anti-HBs during the 6-week off-treatment period.

Figure 6:
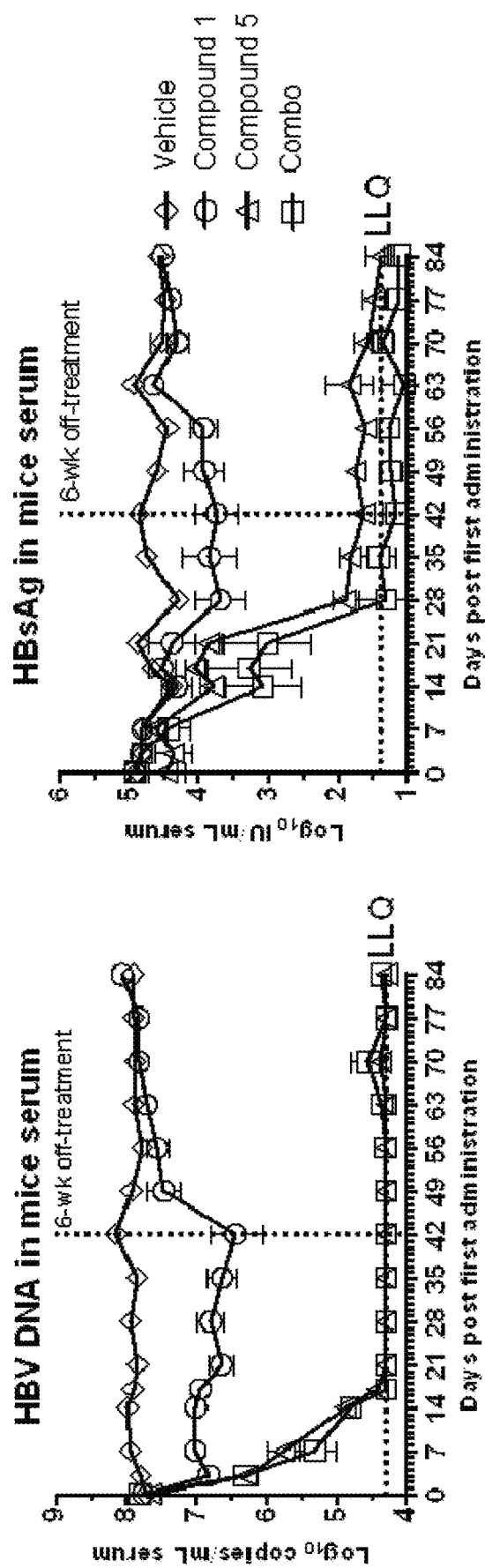
FIG. 6: HBV DNA and HBsAg in the AAV-HBV infected mice treated with vehicle, Compound 1 (100 mg/kg), Compound 5 (12 mg/kg), or the combination of Compound 1 plus Compound 5. The treatment started after the mice were infected with AAV-HBV for 4 weeks. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.

As shown in FIG. 6, Compound 5 is another capsid inhibitor which reduced both HBV DNA and HBsAg. The combination of Compound 5 plus the TLR7 agonist Compound 1 further suppressed HBsAg below the LLQ within 4 weeks post treatment, and the viral reduction was sustained throughout the study even after the treatment was removed for 6 weeks. As shown in FIG. 7, 4 out of 8 mice taking Compound 1 plus Compound 5 developed detectable levels of anti-HBs during the 6-week off-treatment period.

Example 8

A Combination of TLR7 Agonist (Compound 1 and 8) and HBV Capsid Assembly Inhibitor (Compound 4 and 10) Potently Reduced HBV DNA and HBsAg in AAV-HBV Mouse Model In another independent study, more combinations of a TLR7 agonist plus a Capsid inhibitor and corresponding single compound treatments were tested (as summarized in Table 3) using the same AAV-HBV mouse model and methods of measurement of HBV biomarkers described in Example 5.

TABLE 3

Combination study design in AAV-HBV mouse model for Compound 1, 4, 8 and 10

| Group # | Mice# | Compound | Dose (mg/kg) | Drug delivery |
|---|---|---|---|---|
| 1 | 7 | vehicle | 0 | PO, QOD, 42D, |
| 2 | 7 | Compound 1 | 100 | |
| 3 | 7 | Compound 8 | 300 | |
| 4 | 7 | Compound 4 | 20 | PO, QD, 42D |
| 5 | 7 | Compound 10 | 20 | |
| 6 | 7 | Compound 1 | 100 | PO, QOD, 42D |
| | | Compound 10 | 20 | PO, QD, 42D |
| 7 | 7 | Compound 8 | 300 | PO, QOD, 42D |
| | | Compound 4 | 20 | PO, QD, 42D |
| 8 | 7 | Compound 8 | 300 | PO, QOD, 42D |
| | | Compound 10 | 20 | PO, QD, 42D |

In this specific study, seven mice were recruited in each group and animals received the first dose at least 38 days post AAV-HBV infection. The tested combinations included Compound 8 plus Compound 4, Compound 8 plus Compound 10, and Compound 1 plus Compound 10. All compounds were formulated as an inclusion complex with 2% Klucel LF, 0.1% Polysorbate 80, and 0.1% Parabens in water, and an equivalent volume of placebo containing 2% Klucel LF, 0.1% Polysorbate 80, and 0.1% Parabens was used in the vehicle group. Specifically, for the combination of Compound 8 plus Compound 4, 30 mg/mL of Compound 8 and 2 mg/mL of Compound 4 were formulated. The group Compound 8 were orally dosed at 300 mg/kg QOD, while the group Compound 4 were orally dosed at 20 mg/kg QD. And then the corresponding Combo group received 30 mg/kg of Compound 8 QOD plus 20 mg/kg Compound 4 QD. For the combination of Compound 8 plus Compound 10, 30 mg/mL of Compound 8 and 2 mg/mL of Compound 10 were formulated. The group Compound 8 were orally dosed at 300 mg/kg QOD, while the group Compound 10 were orally dosed at 20 mg/kg QD. And then the corresponding Combo group received 300 mg/kg of Compound 8 QOD plus 20 mg/kg Compound 10 QD. For the combination of Compound 1 plus Compound 10, 10 mg/mL of Compound 1 and 2 mg/mL of Compound 10 were formulated. The group Compound 1 was orally dosed at 100 mg/kg QOD, while the group Compound 10 were orally dosed at 20 mg/kg QD. And then the corresponding Combo group received 100 mg/kg of Compound 1 QOD plus 20 mg/kg Compound 10 QD. After the first dose, mice were submandibularly bled (75 µL blood/mouse) twice per week for serum collection until the end of the studies. The collected blood were left at 37° C. for at least 30 minutes to coagulate and then centrifuged at 13,200×g, 4° C. for 3 minutes to obtain mouse serum. These serum samples were subjected to analysis of HBV biomarkers.

Figure 8:
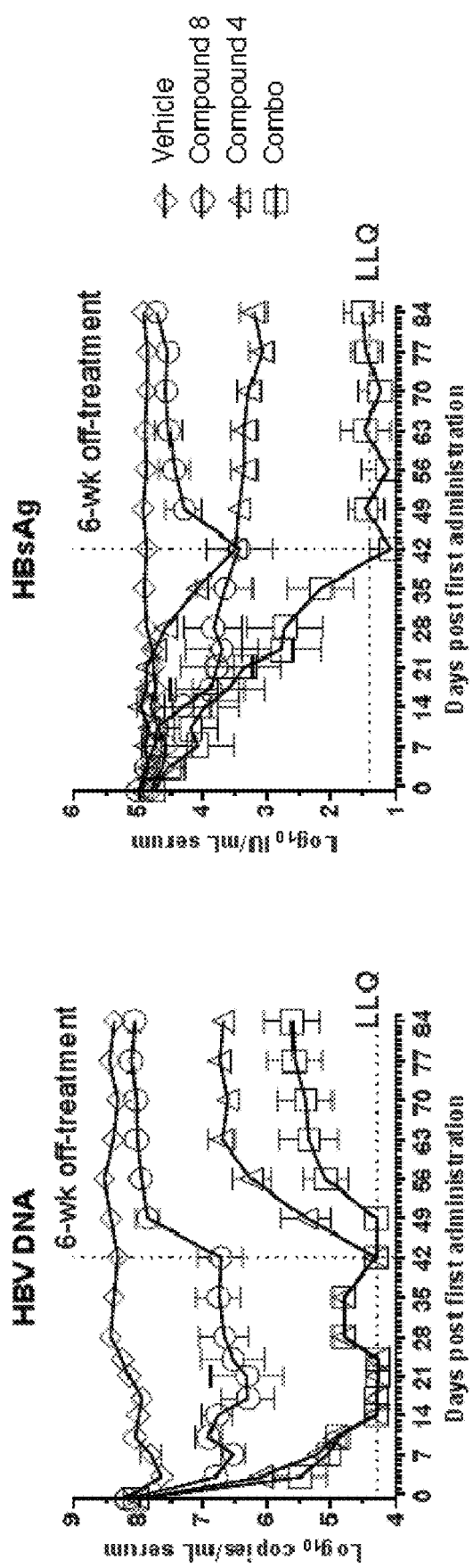
FIG. 8: HBV DNA and HBsAg in the AAV-HBV infected mice treated with vehicle, Compound 8 (300 mg/kg), Compound 4 (20 mg/kg), or the combination of Compound 8 plus Compound 4. The treatment started after the mice were infected with AAV-HBV for at least 38 days. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.
Figure 9:
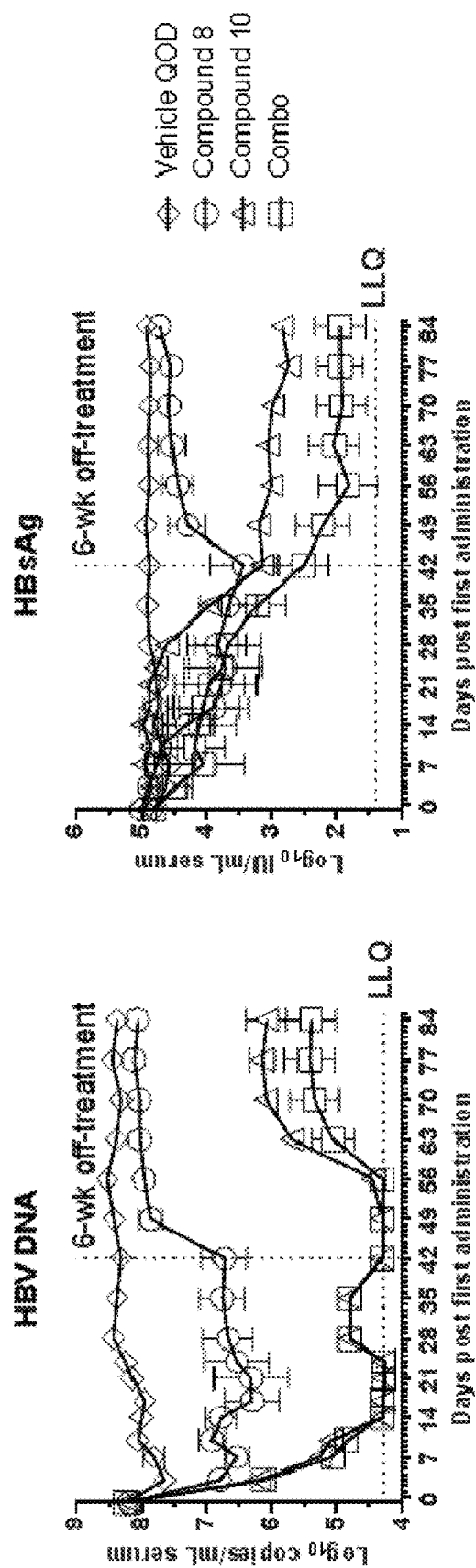
FIG. 9: HBV DNA and HBsAg in the AAV-HBV infected mice treated with vehicle, Compound 8 (300 mg/kg), Compound 10 (20 mg/kg), or the combination of Compound 8 plus Compound 10. The treatment started after the mice were infected with AAV-HBV for at least 38 days. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.
Figure 10:
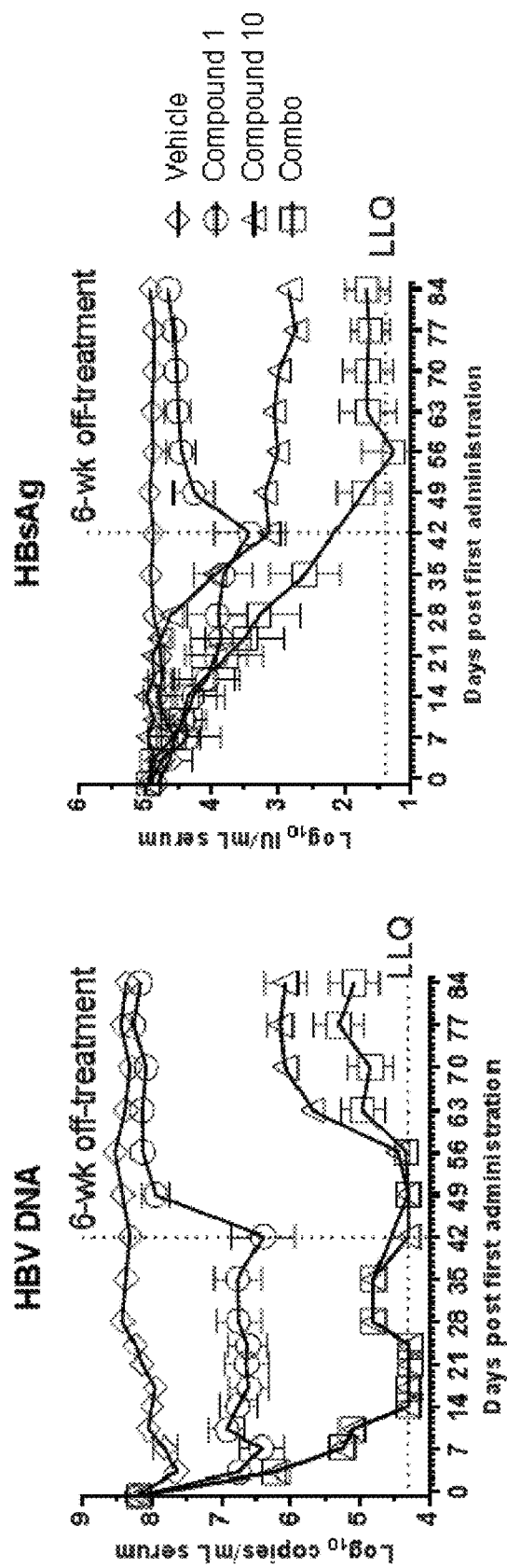
FIG. 10: HBV DNA and HBsAg in the AAV-HBV infected mice treated with vehicle, Compound 1 (100 mg/kg), Compound 10 (20 mg/kg), or the combination of Compound 1 plus Compound 10. The treatment started after the mice were infected with AAV-HBV for at least 38 days. They were given the treatment for 6 weeks, and were monitored for another 6-week off-treatment period. HBV DNA and HBsAg in mouse serum were measured on the indicated time points by RT-qPCR and HBsAg CLIA, respectively. The results were presented as mean±SEM. LLQ: lower limit of quantification.
Figure 11:
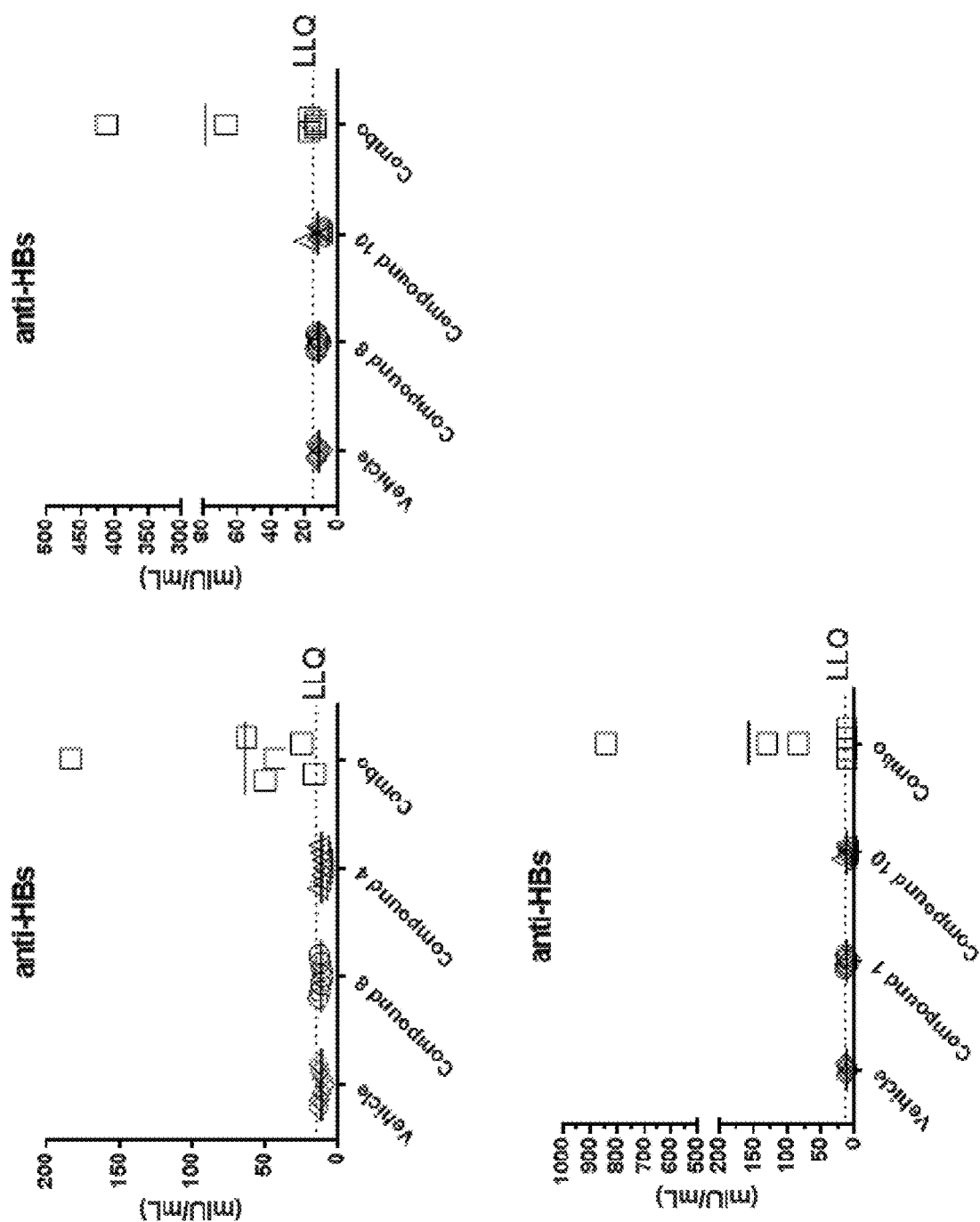
FIG. 11: The level of anti-HBs antibody (antibody against HBsAg) in the serum of each mouse taking the single or combination treatment as described in FIGS. 8, 9, and 10. The serum samples were collected on day 31 post the removal of treatment and anti-HBs was measured by anti-HBs CLIA. LLQ: lower limit of quantification.

The results in FIG. 8 showed that TLR7 agonist Compound 8 alone reduced HBV DNA and HBsAg by about 2-log and 1.5-log respectively at the end of the treatment, while the combination of Compound 8 plus capsid inhibitor Compound 4 further reduced HBsAg to the level below the LLQ. During the 6-week off-treatment period, the combination group demonstrated sustainable HBsAg reduction, minimal HBV DNA rebound, and high levels of anti-HBs which was not seen in vehicle and single treatment groups, as shown in FIG. 11. Such benefits of the combination treatment were also consistently observed in the combination groups of Compound 8 plus Compound 10, and Compound 1 plus Compound 10, as shown in FIGS. 9, 10, and 11.

In summary, the results above have proven for the first time that the combination of a TLR7 agonist plus an HBV Capsid inhibitor is an effective therapy to greatly reduce or even eliminate HBV DNA and HBsAg. After the combination therapy, the viral suppression has been shown to last for as long as 6 weeks without treatment. In most chronically HBV-infected patients, the current available therapies can rarely achieve HBsAg seroconversion due to the fact that most of these therapies are unable to elicit anti-HBs (antibody against HBsAg). In our combination studies, it is striking to find that anti-HBs has become detectable during the 6-week off-treatment period, and this was most evident in the mice taking the combination therapies as shown in FIGS. 7 and 11. Therefore, the combination therapy of a TLR7 agonist plus an HBV Capsid inhibitor offers another key benefit to promote the development of anti-HBs. As sustained HBsAg loss and/or anti-HBs seroconversion is an ideal treatment endpoint for chronic hepatitis B, our combination treatment represents a novel way to achieve clinical cure of chronic HBV infection.

The invention claimed is:

1. A pharmaceutical composition comprising:
a TLR7 agonist and an HBV capsid assembly inhibitor, in a pharmaceutically acceptable carrier,
wherein the TLR7 agonist is a compound of formula (I)

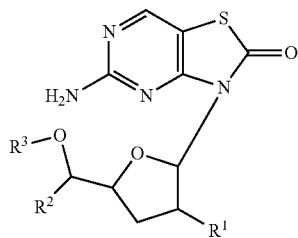

(I)

wherein:
R$^1$ is hydroxy, C$_{1-6}$alkyl, haloC$_{1-6}$alkyl, C$_{1-6}$alkylcarbonyl-O—, C$_{1-6}$alkyl-S—, azido, cyano, C$_{2-6}$alkenyl, C$_{1-6}$alkylsulfonyl-NH—, (C$_{1-6}$alkyl)$_2$N—, C$_{1-6}$alkylcarbonyl-NH— or heterocyclic amino;
R$^2$ is hydrogen, C$_{1-6}$alkyl, C$_{1-6}$alkoxyC$_{1-6}$alkyl, C$_{3-7}$cycloalkyl, C$_{2-6}$alkynyl, C$_{2-6}$alkenyl, benzyl or thiophenyl; and
R$^3$ is hydrogen or C$_{1-6}$alkylcarbonyl;
or a pharmaceutically acceptable salt, enantiomer or diastereomer thereof;
or wherein the TLR7 agonist is a compound of formula (II)

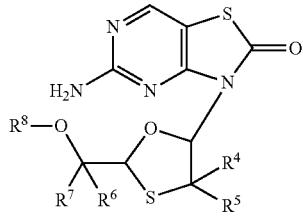

(II)

wherein:
R$^4$ and R$^5$ are independently selected from hydrogen, C$_{2-6}$alkenyl and C$_{1-6}$alkyl;
R$^6$ and R$^7$ are independently selected from hydrogen, C$_{1-6}$alkyl, C$_{3-7}$cycloalkyl, C$_{3-7}$cycloalkylC$_{2-6}$alkynyl, C$_{2-6}$alkenyl, C$_{2-6}$alkynyl and 2-thiophenyl;
R$^8$ is hydrogen or C$_{1-6}$alkylcarbonyl;
or a pharmaceutically acceptable salt, enantiomer or diastereomer thereof;
and wherein the HBV capsid assembly inhibitor is a compound of formula (III)

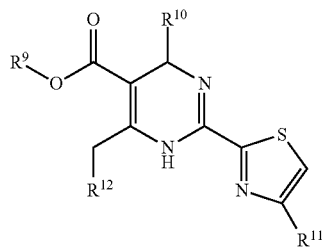

(III)

wherein:
R$^9$ is C$_{1-6}$alkyl;
R$^{10}$ is phenyl substituted with one to three substituents each independently selected from halogen and C$_{1-6}$alkyl;
R$^{11}$ is hydrogen or C$_{1-6}$alkyl; and
R$^{12}$ is monocyclic, bicyclic fused or bicyclic bridged heterocyclyl;
or a pharmaceutically acceptable salt, enantiomer or diastereomer thereof.

2. The pharmaceutical composition of claim 1, wherein the TLR7 agonist is:
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate;
5-amino-3-(3'-deoxy-β-D-ribofuranosyl)-3H-thiazolo[4,5-d]pyrimidin-2-one;
5-amino-3-(2'-O-acetyl-3'-deoxy-β-D-ribofuranosyl)-3H-thiazolo[4,5-d]pyrimidin-2-one;
5-amino-3-(3'-deoxy-β-D-ribofuranosyl)-3H,6H-thiazolo[4,5-d]pyrimidin-2,7-dione;
[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate; or
[(S)-[(2S,5R)-5-(5-amino-2-oxo-thiazolo[4,5-d]pyrimidin-3-yl)-1,3-oxathiolan-2-yl]-cyclopropyl-methyl] acetate;
or a pharmaceutically acceptable salt, enantiomer or diastereomer thereof;
and wherein the HBV capsid assembly inhibitor is:
3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

or a pharmaceutically acceptable salt, enantiomer or diastereomer thereof.

3. The pharmaceutical composition of claim 1, wherein the pharmaceutical composition consists of:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1 S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-chloro-4-fluoro-phenyl)-5-methoxycarbonyl-2-thiazol-2-yl-3,6-dihydropyrimidin-4-ylmethyl]-morpholine-3-carboxylic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H-thiazolo[4,5-d]pyrimidin-2-one and (S)-44(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H,6H-thiazolo[4,5-d]pyrimidin-2,7-dione and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(3'-deoxy-β-D-ribofuranosyl)-3H-thiazolo[4,5-d]pyrimidin-2-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H-thiazolo[4,5-d]pyrimidin-2-one and 2-[(1R,3 S, 5 S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(3'-deoxy-β-D-ribofuranosyl)-3H-thiazolo[4,5-d]pyrimidin-2-one and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(2'-O-acetyl-3'-deoxy-β-D-ribofuranosyl)-3H-thiazolo[4,5-d]pyrimidin-2-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(2'-O-acetyl-3'-deoxy-β-D-ribofuranosyl)-3H-thiazolo[4,5-d]pyrimidin-2-one and 2-[(1R,3 S, 5 S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(2'-O-acetyl-3'-deoxy-β-D-ribofuranosyl)-3H-thiazolo[4,5-d]pyrimidin-2-one and [(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(3'-deoxy-β-D-ribofuranosyl)-3H,6H-thiazolo[4,5-d]pyrimidin-2,7-dione and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H,6H-thiazolo[4,5-d]pyrimidin-2,7-dione and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

5-amino-3-(3'-deoxy-β-D-ribofuranosyl)-3H,6H-thiazolo[4,5-d]pyrimidin-2,7-dione and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

5-amino-3-(3'-deoxy-β-D-ribofuranosyl)-3H,6H-thiazolo[4,5-d]pyrimidin-2,7-dione and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

in a pharmaceutically acceptable carrier.

4. The pharmaceutical composition of claim 1, wherein the pharmaceutical composition consists of:

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 5-amino-3-(2'-O-acetyl-3'-deoxy-β-D-ribofuranosyl)-3H-thiazolo[4,5-d]pyrimidin-2-one and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

in a pharmaceutically acceptable carrier.

5. The pharmaceutical composition of claim 1, wherein the pharmaceutical composition additionally comprises one or more other antiviral agents.

6. The pharmaceutical composition of claim 5, wherein said one or more other antiviral agents are selected from lamivudine, adefovir, tenofovir, telbivudine and entecavir.

7. The pharmaceutical composition of claim 1, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof, and the HBV capsid assembly inhibitor is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

8. The pharmaceutical composition of claim 1, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

9. The pharmaceutical composition of claim 1, wherein the TLR7 agonist is [(S)-[(2S,5R)-5-(5-amino-2-oxo-thiazolo[4,5-d]pyrimidin-3-yl)-1,3-oxathiolan-2-yl]-cyclopropyl-methyl] acetate, or a pharmaceutically acceptable salt thereof, and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6, 8,8a-tetrahydro-1H-imidazo[1,5-a]pyrazin-2-yl]-2,2-dimethyl-propanoic acid, or a pharmaceutically acceptable salt thereof.

10. The pharmaceutical composition of claim 1, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof, and the HBV capsid assembly inhibitor is 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid, or a pharmaceutically acceptable salt thereof.

11. The pharmaceutical composition of claim 1, wherein the TLR7 agonist is [(1 S)-1-[(2S,4R,5R)-5-(5-amino-2-oxo-thiazolo[4,5-d] pyrimidin-3-yl)-4-hydroxy-tetrahydrofuran-2-yl]propyl] acetate, or a pharmaceutically acceptable salt thereof, and the HBV capsid assembly inhibitor is (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid, or a pharmaceutically acceptable salt thereof.

12. The pharmaceutical composition of claim 1, wherein the TLR7 agonist is 5-amino-3-(2'-O-acetyl-3'-deoxy-β-D-ribofuranosyl)-3H-thiazolo[4,5-d]pyrimidin-2-one, or a pharmaceutically acceptable salt thereof, and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

13. The pharmaceutical composition of claim 1, wherein the TLR7 agonist is 5-amino-3-(2'-O-acetyl-3'-deoxy-β-D-ribofuranosyl)-3H-thiazolo[4,5-d]pyrimidin-2-one, or a pharmaceutically acceptable salt thereof, and the HBV capsid assembly inhibitor is (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid, or a pharmaceutically acceptable salt thereof.

14. A kit comprising a TLR7 agonist and an HBV capsid assembly inhibitor in a container,
wherein the TLR7 agonist is:
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate;
[(S)-[(2S,5R)-5-(5-amino-2-oxo-thiazolo[4,5-d]pyrimidin-3-yl)-1,3-oxathiolan-2-yl]-cyclopropyl-methyl] acetate;
5-amino-3-(3'-deoxy-β-D-ribofuranosyl)-3H-thiazolo[4,5-d]pyrimidin-2-one;
5-amino-3-(2'-O-acetyl-3'-deoxy-β-D-ribofuranosyl)-3H-thiazolo[4,5-d]pyrimidin-2-one;
5-amino-3-(3'-deoxy-β-D-ribofuranosyl)-3H,6H-thiazolo[4,5-d]pyrimidin-2,7-dione;
or [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate;
or a pharmaceutically acceptable salt, enantiomer or diastereomer thereof;
and wherein the HBV capsid assembly inhibitor is:
3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;
2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or
(S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;
or a pharmaceutically acceptable salt, enantiomer or diastereomer thereof.

15. The kit of claim 14, wherein the TLR7 agonist and the HBV capsid assembly inhibitor in the container are:
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;
5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or
5-amino-3-(2'-O-acetyl-3'-deoxy-β-D-ribofuranosyl)-3H-thiazolo[4,5-d]pyrimidin-2-one and
(S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid.

16. The kit of claim 14, further comprising a sterile diluent.

17. The kit of claim 14, further comprising a package insert comprising printed instructions for the use of a TLR7 agonist and an HBV capsid assembly inhibitor as a method for treatment or prophylaxis of hepatitis B virus infection.

18. A method for the treatment or prophylaxis of hepatitis B virus infection, the method comprising:
administering to a subject an effective first amount of a TLR7 agonist, or a pharmaceutically acceptable salt, enantiomer or diastereomer thereof; and
a second amount of an HBV capsid assembly inhibitor, or a pharmaceutically acceptable salt, enantiomer or diastereomer thereof;
wherein the TLR7 agonist is:
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate;
[(S)-[(2S,5R)-5-(5-amino-2-oxo-thiazolo[4,5-d]pyrimidin-3-yl)-1,3-oxathiolan-2-yl]-cyclopropyl-methyl] acetate;
5-amino-3-(3'-deoxy-β-D-ribofuranosyl)-3H-thiazolo[4,5-d]pyrimidin-2-one;
5-amino-3-(2'-O-acetyl-3'-deoxy-β-D-ribofuranosyl)-3H-thiazolo[4,5-d]pyrimidin-2-one;
5-amino-3-(3'-deoxy-β-D-ribofuranosyl)-3H,6H-thiazolo[4,5-d]pyrimidin-2,7-dione;
or
[(2R,3R,5 S)-5-[(1 S)-1-acetoxypropyl]-2-(5-amino-2,7-dioxo-6H-thiazolo[4,5-d]pyrimidin-3-yl)tetrahydrofuran-3-yl] acetate;
or a pharmaceutically acceptable salt, enantiomer or diastereomer thereof;
and wherein the HBV capsid assembly inhibitor is:
3-[(8aS)-7-[((4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
2-[(1R,3 S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;
2-[(1 S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or
(S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;
or a pharmaceutically acceptable salt, enantiomer or diastereomer thereof.

19. The method of claim 18, wherein the TLR7 agonist and the HBV capsid assembly inhibitor are:
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(S)-[(2S,5R)-5-(5-amino-2-oxo-thiazolo[4,5-d]pyrimidin-3-yl)-1,3-oxathiolan-2-yl]-cyclopropyl-methyl] acetate and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;
[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and (S)-4-[(R)-6-(2-chloro-4-fluoro-phenyl)-5-methoxycarbonyl-2-thiazol-2-yl-3,6-dihydropyrimidin-4-ylmethyl]-morpholine-3-carboxylic acid;
5-amino-3-(2'-O-acetyl-3'-deoxy-β-D-ribofuranosyl)-3H-thiazolo[4,5-d]pyrimidin-2-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or
5-amino-3-(2'-O-acetyl-3'-deoxy-β-D-ribofuranosyl)-3H-thiazolo[4,5-d]pyrimidin-2-one and (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid.

20. The method of claim 18, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl]acetate, or a pharmaceutically acceptable salt thereof, and the HBV capsid assembly inhibitor is 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

21. The method of claim 18, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof, and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

22. The method of claim 18, wherein the TLR7 agonist is [(S)-[(2S,5R)-5-(5-amino-2-oxo-thiazolo[4,5-d]pyrimidin-3-yl)-1,3-oxathiolan-2-yl]-cyclopropyl-methyl] acetate, or a pharmaceutically acceptable salt thereof, and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

23. The method of claim 18, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof, and the HBV capsid assembly inhibitor is 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid, or a pharmaceutically acceptable salt thereof.

24. The method of claim 18, wherein the TLR7 agonist is [(1S)-1-[(2S,4R,5R)-5-(5-amino-2-oxo-thiazolo[4,5-d]pyrimidin-3-yl)-4-hydroxy-tetrahydrofuran-2-yl]propyl] acetate, or a pharmaceutically acceptable salt thereof, and the HBV capsid assembly inhibitor is (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid, or a pharmaceutically acceptable salt thereof.

25. The method of claim 18, wherein the TLR7 agonist is 5-amino-3-(2'-O— acetyl-3'-deoxy-β-D-ribofuranosyl)-3H-thiazolo[4,5-d]pyrimidin-2-one, or a pharmaceutically acceptable salt thereof, and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid, or a pharmaceutically acceptable salt thereof.

26. The method of claim 18, wherein the TLR7 agonist is 5-amino-3-(2'-O— acetyl-3'-deoxy-β-D-ribofuranosyl)-3H-thiazolo[4,5-d]pyrimidin-2-one, or a pharmaceutically acceptable salt thereof, and the HBV capsid assembly inhibitor is (S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid, or a pharmaceutically acceptable salt thereof.

27. The method of claim 18, wherein the TLR7 agonist and the HBV capsid assembly inhibitor are administered in the same formulation or different formulations.

28. The method of claim 18, wherein the TLR7 agonist and the HBV capsid assembly inhibitor are administered by the same route or different routes.

29. The method of claim 18, wherein the TLR7 agonist and the HBV capsid assembly inhibitor are administered by parenteral or oral administration.

30. The method of claim 18, wherein the TLR7 agonist and the HBV capsid assembly inhibitor are administered simultaneously or sequentially.

31. The method of claim 18, further comprising administering to the subject one or more other antiviral agents.

32. The method of claim 31, wherein said one or more other antiviral agents are selected from lamivudine, adefovir, tenofovir, telbivudine and entecavir.

* * * * *